(12) United States Patent
Strong

(10) Patent No.: US 7,498,038 B2
(45) Date of Patent: Mar. 3, 2009

(54) CHITIN MICROPARTICLES AND THEIR MEDICAL USES

(75) Inventor: Peter Strong, Oxford (GB)

(73) Assignee: CMP Therapeutics Limited, Oxford (GB)

( * ) Notice: Subject to any disclaimer, the term of this patent is extended or adjusted under 35 U.S.C. 154(b) by 71 days.

(21) Appl. No.: 10/779,456

(22) Filed: Feb. 13, 2004

(65) Prior Publication Data

US 2004/0234614 A1 Nov. 25, 2004

Related U.S. Application Data

(63) Continuation-in-part of application No. PCT/GB02/03814, filed on Aug. 16, 2002.

(30) Foreign Application Priority Data

Aug. 16, 2001 (GB) ................................. 0120030.2
Mar. 22, 2002 (GB) ................................. 0206864.1

(51) Int. Cl.
*A61K 39/35* (2006.01)
(52) U.S. Cl. ..................... 424/275.1; 424/493; 424/494
(58) Field of Classification Search ........................ None
See application file for complete search history.

(56) References Cited

U.S. PATENT DOCUMENTS

| 4,873,092 A | 10/1989 | Azuma et al. | |
|---|---|---|---|
| 5,292,513 A | 3/1994 | Gristina et al. | |
| 5,585,106 A | 12/1996 | Gristina et al. | |
| 5,591,441 A | 1/1997 | Gristina et al. | |
| 5,690,954 A | 11/1997 | Illum et al. | |
| 6,080,762 A * | 6/2000 | Allen et al. | 514/337 |
| 2003/0180367 A1 | 9/2003 | Parikh et al. | |

FOREIGN PATENT DOCUMENTS

| WO | 90/09780 | 9/1990 |
|---|---|---|
| WO | 93/15737 | 8/1993 |
| WO | WO 97/20576 | 6/1997 |
| WO | 98/01160 | 1/1998 |
| WO | 98/30207 | 7/1998 |
| WO | 99/01498 | 1/1999 |
| WO | 99/27905 | 6/1999 |
| WO | 99/36075 | 7/1999 |
| WO | 00/56361 | 9/2000 |
| WO | 01/26631 A1 | 4/2001 |
| WO | 02/09674 A2 | 2/2002 |
| WO | 02/28429 A2 | 4/2002 |
| WO | 02/34287 A2 | 5/2002 |
| WO | 02/089839 A1 | 11/2002 |
| WO | 03/086454 A1 | 10/2003 |
| WO | 2005/013891 A2 | 2/2005 |

OTHER PUBLICATIONS

Merck Manual of Diagnosis and Therapy, 17th ed. 1999, p. 1041-1058.*
Sigma Aldrich, Product data sheet for chitin powder C9752, p. 1-2.*
Clinical Report, Pediatrics, 1997, vol. 100(1);143-152 (web based, equivalent top. 1-23, supplied p. 1-23).*
Kim et al., J. Dent. Child 2004, vol. 71., p. 126-130.*
Shibata, Y. et al., "Oral Administration of Chitin Down-Regulates Serum IgE Levels and Lung Eosinophilia in the Allergic Mouse," *The Journal of Immunology*, 164: 1314-21, 2000 (XP-002218084).
Shibata, Y. et al., "Alveolar Macrophage Priming by Intravenous Administration of Chitin Particles, Polymers of N-Acetyl-D-Glucosamine, in Mice," *Infection and Immunity*, 65(5): 1734-41, 1997 (XP-002218085).
Nishimura, K. et al., "Effect of Multiporous Microspheres Derived from Chitin and Partially Deacetylated Chitin on the Activation of Mouse Peritoneal Macrophages," *Vaccine*, 5: 136-140, 1987.
Derwent Accession No. 1994-347060, JP 06 271470.
European Patent Office, Patent Abstracts of Japan, JP 10 279606 (Oct. 20, 1998).
Ozdemir et al. "Treatment with chitin microparticles is protective against lung histopathology in a murine asthma model." Clin Exp Allergy 36: 960-968, 2006.
Leung et al. "Effect of anti-IgE therapy in patients with peanut allergy." N Engl J Med 348: 986-993, 2003.
Barrody et al. "Antiallergic effects of H1-receptor antagonists." Allergy 55(suppl. 64) : 17-27, 2000.
Sampson. "9. Food allergy." J Allergy Clin Immunol 111(suppl. 2) : S540-S547, 2003.
Epstein. "Are mouse models of allergic asthma useful for testing novel therapeutics?" Exp Toxicol Pathol 57 (suppl. 2) : 41-44, 2006.
Merkus et al. Cyclodextrins in nasal drug delivery. Adv Drug Deliv Rev 36: 41-57, 1999.

* cited by examiner

*Primary Examiner*—Eileen B O'Hara
*Assistant Examiner*—Yunsoo Kim
(74) *Attorney, Agent, or Firm*—Frommer Lawrence & Haug LLP; Thomas J. Kowalski; Russell A. Garman

(57) ABSTRACT

The present invention relates to chitin microparticles and their medical uses, in particular in the treatment of allergy, or the treatment of conditions that would benefit from an upregulation of the cell mediated immune system, or an upregulation of natural killer (NK) cell activity and/or the secretion of interferon-γ (IFN-γ).

13 Claims, 19 Drawing Sheets

```
                         SEQUENCE LISTING

<160> NUMBER OF SEQ ID NOS: 1

<210> SEQ ID NO 1
<211> LENGTH: 12
<212> TYPE: PRT
<213> ORGANISM: Aspergillus fumigatus

<400> SEQUENCE: 1

Ala Thr Trp Thr Cys Ile Asn Gln Gln Leu Asn Pro
 1               5                  10
```

CHITIN MICROPARTICLES AND THEIR MEDICAL USES

RELATED APPLICATIONS/PATENTS & INCORPORATION BY REFERENCE

This application is a Continuation-in-Part of PCT/GB02/03814, filed on Aug. 16, 2002, designating the U.S., published on Feb. 27, 2003 as WO 03/015744 A1, and claiming priority from GB Application No. 0120030.2 filed Aug. 16, 2001 and GB Application No. 0206864.1 filed Mar. 22, 2002. All of the above-mentioned applications, as well as all documents cited herein, and documents referenced or cited in documents cited herein, are incorporated herein by reference.

FIELD OF THE INVENTION

The present invention relates to chitin microparticles and their medical uses, in particular in the treatment of allergy, conditions that would benefit from an upregulation of the cell mediated immune system and conditions that would benefit from an up-regulation of natural killer (NK) cell activity and/or the secretion of interferon-$\gamma$ (IFN-$\gamma$).

BACKGROUND OF THE INVENTION

The alveolar macrophage is the most abundant leukocyte in the lumen of the alveolus and is central to the innate immune system of the lung by promoting phagocytic clearance and by the secretion of cytokines that promote an effective cell mediated immune response to inhaled particulates including microbes and pathogens. The principle cytokines produced during phagocytosis are I-12, TNF$\alpha$, and IL-18. These macrophage cytokines subsequently induce IFN-$\gamma$ production by NK cells and Th1 lymphocytes. IFN-$\gamma$ acts synergistically with these cytokines to promote a Th1 cell mediated immune response and also down-regulate the production of Th2 cytokines, in particular IL-4 and IL-5 which are strong mediators of allergy.

Studies by Shibata et al (1-4), have shown that oral delivery of 1-10 $\mu$m phagocytosable chitin particles results in an elevation of Th1 cytokines in mouse spleen cell cultures. The effect was specific to the particulates as no elevation was produced by soluble chitin. It could also be reproduced in 1 $\mu$m polystyrene microspheres coated with N-Acetyl-D-Glucosamine, which is the main component of chitin. It was also demonstrated that oral administration of chitin down-regulates serum IgE and lung eosinophilia in a murine model of ragweed allergy (1).

Shibata et al have also developed a mouse model of allergic airway inflammation and orally administered chitin preparations to the mice (Shibata 2000). Ragweed-specific IgE levels were significantly reduced after daily oral administration of chitin to ragweed-sensitised mice, before and during immunisation. Bronchioalveolar lavage (BAL) cells were harvested 14 days after immunisation and a reduction in the levels of eosinophil and lymphocyte levels was observed after chitin treatment. Lung inflammation was determined histologically 14 days after immunisation and the peribronchial, perivascular and total lung inflammation were inhibited in the chitin-treated group.

When chitin was administered prophylactically to mice who were subsequently administered ragweed, IL-4, IL-5 and IL-10 production was significantly reduced and low but significant levels of IFN-$\gamma$ were detected.

Chitin also has a prophylactic effect when administered to C57BL6 mice, which are higher responders for cell-mediated immunity/Th1 responses, but lower responders for allergic responses compared with BALB/c mice.

When ragweed-sensitised mice were treated simultaneously with ragweed and chitin, the levels of IL IL-5 and IL-10 produced were significantly reduced compared to those stimulated by ragweed alone.

However, while Shibata et al disclose the use of chitin microparticles for the treatment of allergy, the compositions are administered orally as a supplement to activate macrophages and prophylactically strengthen the immune system in the absence of recurrent bacterial infections that are decreasingly common in industrialised countries.

Japanese Patent Application No: 19997-0087986 A (Unitika Limited) discloses the use of deacetylated chitin particles in the form of powders, granules or fibres for delivery to the nasal mucosa. The chitin particles have an effective particle diameter of 20 to 250 microns and are proposed for the treatment of allergic symptoms at an inflammatory site such as pollinosis.

U.S. Pat. No. 5,591,441 (Medical Sciences Research Institute) concerns the use of particulate compositions for providing protection against microorganism infection and biological warfare agents. The compositions are delivered intravenously with the aim of providing a short lived increased in in vivo peroxide levels to kill the microorganisms.

More generally, existing treatments for allergies typically involve the use of steroids to depress the immune system. There are undesirable side effects with steroid therapy. Synthetic drugs, such as steroids are expensive to manufacture, involving a complex process which requires complex quality control and GMP standards to meet requirements of Health and Safety Authorities. In view of these factors, it remains a problem in the art in finding effective treatments for allergy.

*Pseudomonas aeruginosa*, an opportunistic pathogen, is a leading cause of life threatening infections in immuno-compromised individuals and is a major risk to patients on ventilator support and many disease conditions in which there is a reduction in lung function and a reduced ability to clear infections. Each year, over two million patients die as a result. A report on the incidence of hospital-associated infections places *P. aeruginosa* among the three most frequently reported pathogens (5). *P. aeruginosa* is also a common cause of chronic and life threatening pulmonary infection in cystic fibrosis patients. Recent reports list *P. aeruginosa* among the most serious antibiotic-resistant bacteria and one for which effective vaccines are needed (6). *Streptococcus pneumoniae* is a ubiquitous pathogen and responsible for a high proportion of cases of pneumonia (both lobar and bronchopneumonia) and one of the leading causes of illness and death among young children, the elderly and those with an impaired immune system as the result of diseases, such as AIDS, or immunosuppressive therapy, such as for bone marrow transplantation. The invasive form of *Streptococcal* infection, in which the bacteria disseminate into the blood and other organs leads to very serious complications. Each year in the United States, pneumococcal disease is estimated to cause 3000 cases of meningitis, 50,000 cases of bacteraemia, 125,000 hospitalisations and 6,000,000 cases of Otitis media.

There is a growing concern about the emergence of antibiotic resistant strains of *S. pneumoniae* and there is a considerable amount of research into new treatments and vaccines.

SUMMARY OF THE INVENTION

Broadly, the present invention relates to the use of chitin microparticle (CMP) preparations for treating disorders by delivering the microparticles intranasally to the sinuses and upper respiratory tract, e.g. using an intranasal spray, or by inhalation, e.g. targeting alveolar macrophages in the lungs. The chitin microparticle compositions are different to many of those disclosed in the prior art, typically having particle sizes of less than 10 μm.

The macrophage has a central control function in the innate immune system of the lung by promoting phagocytic clearance of particles and by processing the presentation of inhaled allergens to lymphocytes and by secretion of cytokines that promote an effective cell mediated immune response to inhaled particulates including microbes and allergenic substance. In particular, the present invention discloses that intranasal delivery of chitin microparticles is particularly effective in reducing a number of parameters indicative of inflammation, thus providing an alternative to steroid treatments.

The work disclosed herein arises from the finding that the intranasal delivery of chitin microparticles to mouse models of allergy produced by *Aspergillus fumigatus* (Afu) and *Dermatophagoides pteronyssinus* (Der p) is particularly effective in reducing levels of peripheral blood eosinophilia, serum total IgE, Afu-specific IgG1, the cytokine IL-4, GM-CSF, and airway hyperresponsiveness (AHR), as well as increasing levels of the cytokines IL-12, IFN-γ and TNF-α. Intranasal pre-treatment of chitin microparticles was effective in preventing the progression of infection by *P. aeruginosa* or *S. pneumoniae* in mice infected with these pathogens. In addition, CMP have been shown to enhance the TNFα and IFN-γ response of activated human leukocytes.

Accordingly, in a first aspect, the present invention provides a method of treating an allergy in a patient in need thereof, comprising administering to the patient a therapeutically effective amount of a chitin microparticle (CMP) preparation, wherein the CMP preparation is administered intranasally or by inhalation.

In an alternative aspect, the present invention provides a method of treating a condition in a patient in need thereof, wherein the condition would benefit from the up-regulation of the cell-mediated immune system, the method comprising administering to the patient a therapeutically effective amount of a chitin microparticle (CMP) preparation, wherein the CMP preparation is administered intranasally or by inhalation.

In a further aspect, the present invention provides a method of treating a condition in a patient in need thereof, wherein the condition is treatable by up-regulation of the activity of NK cells and/or secretion of IFN-γ by cells of the immune system, the method comprising administering to the patient a therapeutically effective amount of a chitin microparticle (CMP) preparation, wherein the CMP preparation is administered intranasally or by inhalation.

In yet another aspect, the present invention provides a delivery device for the administration of a chitin microparticle (CMP) composition comprising a) a reservoir of chitin microparticles; b) a delivery orifice adapted to locate in a patient's mouth or nose; and c) a valve between the reservoir and the delivery orifice such that the valve can be operated to control delivery of the chitin microparticles.

In a still further aspect, the present invention provides a method for up-regulating the cell-mediated immune system, or the activity of NK cells, and/or the secretion of IFN-γ by cells of the immune system, comprising administering to a patient a therapeutically effective amount of a chitin microparticle (CMP) preparation, wherein the CMP preparation is administered intranasally or by inhalation.

BRIEF DESCRIPTION OF THE FIGURES AND TABLES

Figure 1:
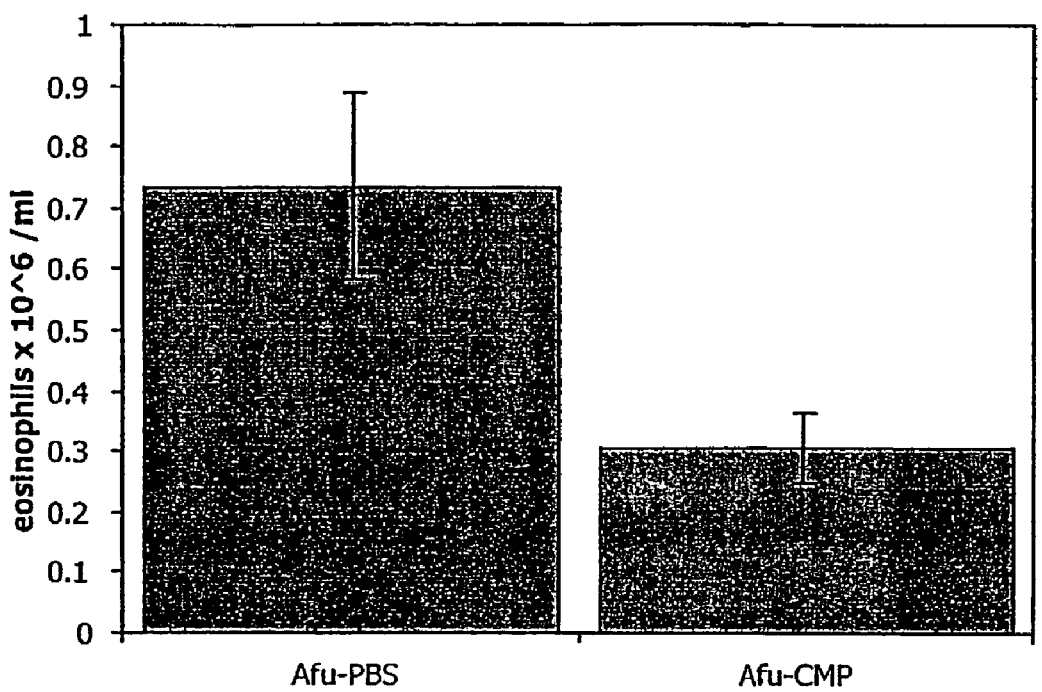
FIG. 1 shows the results of treatment of Afu challenged mice, with 17 μg CMP which produced a significant decrease ($p<0.05$) in peripheral blood eosinophilia.

Table 1a indicates increases in the cytokines IL-12, IFNγ and TNFα in spleen cells of mice challenged with Der p and Afu allergens, in response to treatment with CMP.

Table 1b indicates an increase in the cytokine GM-CSF in spleen cells of mice challenged with Der p, in response to treatment with CMP.

Table 1c indicates a decrease in the geometric mean fluorescence of the cytokine IL-4 in response to treatment with CMP.

DETAILED DESCRIPTION

The present invention relates to the use of chitin microparticle (CMP) preparations for treating disorders by delivering the microparticles intranasally to the sinuses and upper respiratory tract, e.g. using an intranasal spray, or by inhalation, e.g. targeting alveolar macrophages in the lungs. The chitin microparticle compositions of the present invention are different to many of those disclosed in the prior art, typically having particle sizes of less than 10 μm.

The methods of the present invention are useful in the treatment of allergy, and in the treatment of other conditions where it is desirable to up-regulate cell-mediated immune system response, or up-regulate the activity of NK cells, and/or the secretion of IFN-γ by cells of the immune system.

In this disclosure, "comprises," "comprising," "containing" and "having" and the like can have the meaning ascribed to them in U.S. Patent law and can mean "includes," "including," and the like. "Consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

In one aspect, the present invention provides the use of a chitin microparticle (CMP) preparation, composition or medicament for treating an allergy or other condition, wherein the medicament is delivered intranasally or by inhalation.

In an alternative aspect, the present invention provides a method of treating a patient suffering from an allergy or other condition, the method comprising administering to a patient in need thereof a therapeutically effective amount of a chitin microparticle preparation, wherein the CMP preparation is administered intranasally or by inhalation.

Accordingly, the present invention provides a method of treating an allergy in a patient in need thereof, comprising administering to the patient a therapeutically effective amount of a chitin microparticle (CMP) preparation, wherein the CMP preparation is administered intranasally or by inhalation.

In an alternative aspect, the present invention provides a method of treating a condition in a patient in need thereof, wherein the condition would benefit from the up-regulation of the cell-mediated immune system, the method comprising administering to the patient a therapeutically effective amount of a chitin microparticle (CMP) preparation, wherein the CMP preparation is administered intranasally or by inhalation.

In a further aspect, the present invention provides a method of treating a condition in a patient in need thereof, wherein the condition is treatable by up-regulation of the activity of NK cells and/or secretion of IFN-γ by cells of the immune system, the method comprising administering to the patient a therapeutically effective amount of a chitin microparticle (CMP) preparation, wherein the CMP preparation is administered intranasally or by inhalation.

In yet another aspect, the present invention provides a delivery device for the administration of a chitin microparticle (CMP) composition comprising a) a reservoir of chitin microparticles; b) a delivery orifice adapted to locate in a patient's mouth or nose; and c) a valve between the reservoir and the delivery orifice such that the valve can be operated to control delivery of the chitin microparticles.

In a still further aspect, the present invention provides a method for up-regulating the cell-mediated immune system, or the activity of NK cells, and/or the secretion of IFN-γ by cells of the immune system, comprising administering to a patient a therapeutically effective amount of a chitin microparticle (CMP) preparation, wherein the CMP preparation is administered intranasally or by inhalation.

The term "patient", as used herein, refers to any human or non-human animal in need of treatment. In preferred embodiments the patient is a human. In other embodiments the patient may be a non-human animal. Non-human animals that can be treated using the methods of the present invention include livestock species and pets.

Conditions that can be treated using the methods of the present invention include allergies and other non-allergic conditions. Examples of allergies that can be treated according to the methods of the present invention include seasonal respiratory allergies, commonly referred to as hay fever; allergy to aeroallergens including house mite dust, fungal spores, grass pollens, tree pollens and animal danders; allergy treatable by reducing serum IgE and eosinophilia; asthma; eczema and food allergies; dermatitis such as atopic dermatitis.

The present invention provides a composition comprising a chitin microparticles composition and an allergen. These compositions can be employed in the treatment of allergies and allergic symptoms, such as anaphylactic shock, which are associated with conventional desensitisation therapy.

Oral application of IL-12 has been shown to suppress anaphylactic reactions and so administering an allergen with a CMP composition should help to moderate the anaphylactic reactions arising during desensitisation therapy designed to build up tolerance to an allergen. Allergens can be readily extracted from food and are commercially available as they are used in the diagnosis and treatment of allergy. One particular application of this aspect of the invention is in the treatment of food allergy. Examples of common food allergens include milk, wheat, gluten, eggs, nuts or shellfish, and the skilled person will be able to formulate these with the CMP composition for delivery to a patient.

In an alternative aspect, the present invention provides a kit comprising:
(a) a chitin microparticle composition; and
(b) an allergen; for simultaneous or sequential administration to a patient.

One further specific embodiment involving the treatment of allergy is in the treatment of horses, and particularly thoroughbred horses, which have a tendency to suffer from allergic conditions such as asthma or recurrent lung infections.

In a further aspect, the present invention provides the use of a chitin microparticle (CMP) preparation for the preparation of a medicament for the treatment of conditions that would benefit from the up-regulation of the cell-mediated immune system, wherein the medicament is administered intranasally or by inhalation.

In an alternative aspect, the present invention provides a method of treating a patient suffering from a condition that would benefit from the up-regulation of the cell-mediated immune system, the method comprising administering to a patient in need thereof a therapeutically effective amount of a chitin microparticle preparation, wherein the CMP preparation is administered intranasally or by inhalation.

Thus, in this aspect of the invention, the CMP composition can be used to strengthen the immune system of an individual. Conditions that benefit from the up-regulation of the cell-mediated immune system include the treatment of microbial infections, including bacterial infections, fungal infections and viral infections, particularly among vulnerable patient groups such as the elderly, premature babies, infants, transplantation patients, immunosuppressed patients such as chemotherapy patients, hospital patients at risk of opportunistic infection, patients on ventilators, cystic fibrosis patients and patients with AIDS. The invention is particularly applicable to the treatment of ear, nose, throat and lung infections.

Specific examples of bacterial infection include the treatment of infection by microorganisms such as *Pseudomonas aeruginosa, Streptococcus* species such as *Streptococcus pneumoniae, Streptococcus pyrogenes, Streptococcus agalactiae, Haemophilus influenza, Klebsiella pneumoniae, Yersinia enteocolitica, Salmonella, Listeria*, Mycobacterial infections including *Mycobacterium tuberculosis, Mycobacterium leprae*, parasitic infections including *Leishmania* species and *Schistosoma* species.

One condition caused by microbial infection, typically by *Streptococcus pneumoniae*, is recurrent ear infections such as Otitis media. These conditions occur in children and adults and are currently treated using antibiotics. It would be advantageous to use the chitin microparticle compositions of the invention to treat these conditions and reduce the need for antibiotics.

The preparations of the invention can be used in the treatment of tuberculosis either to treat an existing infection or to protect vulnerable patient groups from infection.

Other examples of microbial infections include bacterial pneumonias, such as ventilator-associated pneumonia, and cystic fibrosis associated infections.

Examples of fungal infections include fugal infections such as invasive pulmonary aspergillosis and invasive pulmonary candidiasis, *Pneumocystis carinii* pneumonia, *Coccidioides* and *Crytococcus* infections, e.g. in immunosuppressed patients.

Examples of viral conditions treatable according to the present invention include pulmonary viral infections such as respiratory syncytial virus bronchiolitis, especially in infants and the elderly, or influenza virus, or rhino virus. Numerous studies have shown that during the progression of AIDS, mononuclear cells lose their ability to secrete IL-2, IL-12 and IFN-γ and produce increased levels of IL-4, which allows the HIV virus to proliferate. Therefore treatment with CMP, given intranasally or by inhalation, will be useful in reducing the progression of HIV infection by restoring IL-12 and IFN-γ levels.

In a further aspect, the present invention provides the use of a chitin microparticle (CMP) preparation for the preparation of a medicament for the treatment of conditions treatable by up-regulation of the activity of NK cells and/or secretion of IFN-γ by cells of the immune system, wherein the medicament is administered intranasally or by inhalation.

In an alternative aspect, the present invention provides a method of treating a patient suffering from a condition treatable by up-regulation of the activity of NK cells and/or secretion of IFN-γ by cells of the immune system, the method comprising administering to a patient in need thereof a therapeutically effective amount of a chitin microparticle preparation, wherein the CMP preparation is administered intranasally or by inhalation.

An example of a condition treatable in this aspect of the invention is cancer, and especially lung cancer, lung carcinoma or nasal-pharyngeal carcinoma.

Preferably, the medicaments set out above are for administration to humans. Preferred patient groups for intranasal treatment with CMP would include those suffering from seasonal allergic rhinitis and sinusitis, or chronic respiratory allergies such as house dust mite allergy and who are currently taking steroids or antihistamines. Other groups include hospitalized patients being treated for chronic lung disorders including infections and lung carcinomas.

Chitin is a polymer of N-acetyl-D-glucosamine and has a similar structure to cellulose. It is an abundant polysaccharide in nature, comprising the horny substance in the exoskeletons of crab, shrimp, lobster, cuttlefish, and insects as well as fungi. Any of these or other sources of chitin are suitable for the preparation of CMP preparations for use according to the present invention. In addition to chitin, chitin derivatives can be used in the preparation of microparticles. One such derivative known in the art is chitosan. Chitosan is a de-acetylated form of chitin and occurs naturally in some fungi, and, like chitin, is insoluble in water, see, for example, U.S. Pat. No. 6,638,918, the contents of which are hereby incorporated herein by reference.

There are currently many methods known in the art for extracting natural chitin from the exoskeletons of marine crustaceans and other natural sources, and any such method can be used in accordance with the methods of the present invention. References illustrative of the prior art methods of separating, extracting and purifying the chitin from shellfish include: Chang & Tsai, 1997, "Response Surface Optimization and Kinetics of Isolating Chitin from Pink Shrimp Shell Waste", J. Agric. Food Chem., Vol. 45, pgs 1900-1904; Kawaguti, '62, "Electron Microscopy of the Integumental Structure and its Calcification during Molting in a Crayfish", Biol. J. Okayama, Univ., Vol. 8, pp. 43-58; No & Myers, 1995, "Preparation and Characterization of Chitin and Chitosan—A Review, J. Aquatic Food Product Technol. Vol. 4, pp 27-41; Roer & Dillamen, 1984, "The Structure and Calcification of the Crustacean Cuticle", Amer. Zool., Vol. 24, pp 893-909; Waterman, T. H. '60, "Metabolism and Growth", Vol. 1 in "The Physiology of Crustacea", Acad. Press, p. 449, as cited in U.S. Pat. No. 4,199,496, Col. 3.; and U.S. Pat. Nos. 4,066,735, 4,199,496, 4,293,098, 5,053,113, 5,210,186, the contents of which are hereby incorporated herein by reference.

If the chitin to be used is derived from a natural source, the chitin may be effectively separated from other non-chitinous materials located therein such as lipids, protein, and calcium carbonate. Since chitin is insoluble in virtually everything except highly concentrated acidic solutions, one conventional practice known in the art is to remove the unwanted non-chitinous contaminants from the insoluble chitin matrix by using strong acidic solutions. Examples of prior art methods to accomplish the separartion of chitin from non-chitinous material include are described in U.S. Pat. Nos. 5,210,186, 5,053,113, 4,066,735, and 4,199,496, the contents of which are incorporated herein by reference.

Chitin may also be produced in vitro using chitin synthase enzymes that catalyze the polymerization of N-acetylglucosaminyl residues into chitin from uridine 5'-diphospho-N-acetylglucosamine. Such methods are known in the art, see for example, published U.S. Patent Application No. 20030166235 A1.

In addition to the above methods, chitin can be obtained in pre-purified form from any commercial source.

Preferably, chitin is produced by physically reducing it, e.g. by sonication or milling, to particles having a diameter of less than 50 µm, more preferably less than 40 µm, still more preferably less than 20 µm, more preferably less than 10 µm and most preferably less than 5 µm. As we have found that the effects caused by chitin microparticles are size dependent, it is preferred that the chitin microparticles have average diameters which are less than 10 µm. An upper limit of chitin particles size may be functionally defined by macrophages not recognising the particles. The lower size limit is less important, but preferably the particles are at least 1 µm in diameter. The lower size limit is functionally defined by the chitin particles becoming soluble and hence also not being recognised by macrophages. Particles size and size distribution can readily be determined by the skilled person for example using flow cytometry or a microscope. Methods suitable for the detection of particles and the determination of particle size by flow-cytometry are known in the art, see for example, U.S. Pat. Nos. 4,765,737, 5,444,527, and 6,549,275, the contents of which are hereby incorporated herein by reference. Alternatively or additionally, the chitin microparticles can be made by coating carrier particles, e.g. formed from a biocompatible material such as polystyrene or latex, with N-Acetyl-D-Glucosamine, chitin or a fragment thereof, to form particles having the sizes as defined above, and these compositions are included within the term chitin microparticle composition as used herein.

It should be recognized that in a composition, the chitin microparticles will have a distribution of sizes, typically a normal distribution, and that not all particles within a population will necessarily meet these size limits. However, within a population of chitin microparticles forming a CMP preparation, preferably at least 60%, more preferably at least 75%, more preferably at least 90%, and more preferably 95% and most preferably at least 99%, of the chitin particles have a size distribution within the limits set out above.

The CMP preparations can be delivered to the nasal and/or oral passageways using any suitable method and/or device known in the art. Many nasal and oral delivery pumps, inhalers, sprays and the like are known in the art, and any such device can be used to deliver the CMP particles of the present invention. See for example, U.S. Pat. Nos. 6,644,305, 6,418,9246, and 6,435,179, the contents of which are hereby herein incorporated by reference.

In one aspect, the present invention provides a delivery device comprising a reservoir of chitin microparticles as defined herein, and a delivery orifice adapted to locate in a patient's mouth or nose, wherein the patient can place the delivery orifice in the mouth or nose to administer the chitin microparticles. In some embodiments the device may comprise a valve between the reservoir and the delivery orifice, such that the valve can be operated to control delivery of the chitin microparticles. The microparticles may be drawn into the nose to the sinuses and upper respiratory tract or through the mouth to the alveolar macrophages by inhalation and/or by a propellant. A particularly preferred form of device is a nasal spray bottle containing a CMP preparation and optionally a carrier, the spray bottle having a neck adapted for nasal delivery.

In addition to chitin microparticles, the CMP preparations can comprise one or more of a pharmaceutically acceptable excipient, carrier, propellant, buffer, stabiliser, isotonicizing agent, preservative or anti-oxidant or other materials well known to those skilled in the art. Such materials should be non-toxic and should not interfere with the efficacy of the active ingredient. Preservatives are generally included in pharmaceutical compositions to retard microbial growth, extending the shelf life of the compositions and allowing multiple use packaging. Examples of preservatives include phenol, meta-cresol, benzyl alcohol, para-hydroxybenzoic acid and its esters, methyl paraben, propyl paraben, benzalconium chloride and benzethonium chloride. Preservatives are typically employed in the range of about 0.1% to 1.0% (W/V). Preferably, the pharmaceutically compositions are given to an individual in a "prophylactically effective amount" or a "therapeutically effective amount" (as the case may be, although prophylaxis may be considered therapy), this being sufficient to show benefit to the individual, e.g. providing alleviation of allergy or another condition or prophylaxis for an acceptable period. Typically, this will be to cause a therapeutically useful activity providing benefit to the individual. The actual amount of the compounds administered, and rate and time-course of administration, will depend on the nature and severity of the condition being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980 and Remington's Pharmaceutical Sciences, 19th edition, Mack Publishing Company, 1995. The determination of an appropriate dosage, a "therapeutically effective amount" or a "prophylactically effective amount" is well within the capabilities of one skilled in the art. Furthermore, standard texts such as Remington: The Science and Practice of Pharmacy, $17^{th}$ edition, Mack Publishing Company, incorporated herein by reference, can be consulted to determine a suitable dose for administration, without undue experimentation. It is envisaged that in some situations, the effective amount will be determined by a physician or a member of the emergency services on a case-by-case basis. In other situations, a predetermined amount will be administered, either by a doctor, other medical worker, or even by the contaminated individual themselves. The effective amount may be administered in one or more doses. Administrations can be conducted as frequently as is needed until the desired outcome, such as for example, until the alleviation, of allergy symptoms is achieved.

The compositions of the present invention are preferably administered in dosages of between about 0.01 and 100 mg of active compound per kg of body weight, and more preferably between about 0.5 and 10 mg/kg of body weight. By way of example, this could be achieved using a nasal delivery bottle to deliver 4-8 doses of approximately 0.25 ml of a 5 mg/ml solution of CMP particles.

Embodiments of the present invention will now be described by way of example and with reference to the accompanying figures, however the present invention is not limited to any example described herein.

EXAMPLES

Materials and Methods

Chitin microparticles delivered intranasally represent a new approach to stimulating cell mediated immunity and promoting anti-inflammatory responses in inflamed tissues. The present invention has the considerable advantage that macrophages of the upper respiratory tract or alveolar macrophages can be directly targeted with chitin microparticles of the correct size using an intranasal spray and inhalation delivery respectively.

Two models of allergy, a model of pathogenic lung infection and a model of bacterial infection have been established in the mouse. In addition, an in vitro assay utilizing human monocytes or lymphocytes has been developed, in order to demonstrate the efficiency of the present invention.

The parameters measured in the allergy models are serum IgE and IgG1, peripheral blood eosinophilia, and AHR, which are all significantly elevated in the mouse models of allergy to Afu and Der p allergens and are all significantly reduced by intranasal treatment with CMP. Levels of the cytokines IL-1 2, IFN-γ and TNFα which are reduced in the mouse model of allergy to Der p are all increased by intranasal treatment with CMP and levels of GM-CSF and IL-4 are reduced. The proposed mode of action is that the CMP are bound by the mannose receptors of macrophages in the nasal mucosa and alveolae, which stimulates macrophages and dendritic cells to generate IL-12, TNFα and IL-18, and reverses the suppression of IL-12 produced by allergen challenge, returning the levels to those observed in non-allergic mice. This leads to the generation of IFN-7 by NK cells and Th1 lymphocytes. The reduction in GM-CSF and IL-4 is indicative of a modulation of the immune response from Th2 to Th1. In fact, all these cytokines and particularly IFN promote a shift in the populations of T lymphocytes from Th2 to Th1. GM-CSF is a Th2 cytokine that promotes the differentiation, activation and survival of eosinophils. This culminates in the observed reduction in serum IgE and eosinophilia, which are major components in allergy.

In the mouse model of pathogenic lung infection the survival of mice pre-treated with CMP was measured over 10 days in response to infection with *P. aeruginosa*. Mice pre-treated with CMP showed a significantly improved survival rate over mice which received no pre-treatment with CMP.

In the mouse model of bacterial infection the time-course for the clearance of *S. pneumoniae* from the lungs of infected mice was measured over 24 h. Mice pre-treated with CMP showed significantly ($p<0.001$) lower bacterial colony forming units (cfu) in the lungs compared to PBS pre-treated mice. The time-course for the appearance of *S. pneumoniae* in the blood was measured over 48 h and blood bacteraemia in CMP pre-treated mice was significantly less at 24 h ($p<0.005$) and 48 h than that of PBS pre-treated mice.

The production of TNFα in response to LPS stimulation was measured in human monocytes and IFNγ levels were measured in human T-lymphocytes in response to PMA/Ionomycin stimulation. In both assays, the addition of CMP enhanced cytokine production. This effect, observed in human cells, is consistent with the concept that CMP prime monocytes and phagocytes through binding to the mannose receptor or other carbohydrate receptors, followed by phagocytosis of the CMP. Activation by a microbial product such as lipo-polysaccharide (LPS), enhances the responsiveness of these monocytes, an effect mediated by phagocyte-derived cytokines such as IL-12. CMP can also promote the activity of Th1 lymphocytes, consistent with the concept that CMP promotes a Th1 cell mediated immune response.

Chitin Microparticle Suspension Preparation (CMP)

Chitin microparticles were prepared from purified chitin (Sigma-Aldrich, Poole, UK) by sonication of a suspension of 10 mg/ml in endotoxin free PBS at maximum output for 20 min with cooling on ice every 5 min. The slurry was centrifuged at 1000×g for 10 min to remove large particles and the microparticles were collected by centrifugation at 4000×g and washed 3 times with PBS to remove any solubilized chitin. The supernatant contained a uniform suspension of small particles as judged by light microscopy using a haemocytometer with 50 μm squares and were comparable in size to Ipm latex spheres (Polysciences, Inc., Warrington, Pa., USA). Particles less than 5 μm in diameter were quantified with a Celltac Hematology Analyser (Nihon Kohden, Inc.). Preparations were found to contain 99.9% microparticles less than 5 μm in diameter and at a concentration in the order of $10^{11}$/ml. Endotoxin was measured by Limulus Amebocyte Lysate Assay (BioWhittaker Co,) and shown to be <1 EU/ml.

Mouse Models of Allergy

Allergen Extracts

*Aspergillus fumigatus* (Afu) was grown in a synthetic medium (M199, Sigma Chemicals) as a stationary culture for 1 week at 37° C. Arrunda et al, demonstrated that the expression of Asp f1, a major allergen, is maximal after 1 week and tends to diminish during longer incubation periods (7). The 1 week culture was killed by adding 0.1% Thimerosal for 12 hours. The culture was filtered through glass wool and finally through a 0.45 μm membrane to remove all particulates and possible spores and then dialysed with 3 buffer changes against water. The dialysate was lyophilised to give a brown powder.

A major band at 18 kDa' corresponds to Asp f 1. A band corresponding to Asp f 2 (37 kDa) is also evident. The 18 kDa band was N-terminal sequenced giving the sequence ATWTCINQQLNP (SEQ ID NO: 1) corresponding to the N-terminal sequence for Asp f 1.

It was also demonstrated by ELISA that the 1-week culture filtrate (1 wcf) was recognised by human serum from Afu allergic patients obtained from the National Institute of Biological Standards and Control.

Standardized *Dermatophagoides pteronyssinus* (Der p) extract (Greer Labs, Lenoir, N.C., USA) containing 10000 Allergy Units (AU)/ml was diluted into sterile endotoxin free PBS.

Sensitization

Female C57BL/6 mice were sensitised by 4 weekly i.p. injections of a mixture of allergen extract (68 AU Der p; 200 μg Afu) with alum in 100 μl of sterile PBS.

Allergen Challenge and Treatment with CMP

Sensitized mice were anaesthetized with isoflurane and challenged with 50 allergy units of Der p extract, or 10 μg Afu allergen extract, in PBS given intranasally followed by intranasal doses of PBS or CMP or a particulate control (PC) of 1 μm polystyrene beads in 50μl given 1-2 hours later. In a separate experiment it was shown that approximately 50% of FITC-labelled micro-beads given intranasally could be recovered from the lungs after 30 min.

Peripheral Blood Eosinophils

Blood was collected from the tail vein of the mice (n=4-8/group) for estimation of eosinophils. The total leukocyte count was determined by an automatic cell counter and the proportion of eosinophils was determined by differential counting of May-Grunwald-Giemsa stained blood smears. Results are expressed as $10^6$ cells/ml.

Serum IgE and Afu-specific IgG1

Total serum IgE was measured by sandwich ELISA (BD PharMingen, Cowley, UK) in blood serially diluted from a maximum dilution of 1:20 to give values, which were linear with respect to a standard curve of mouse IgE. Results are expressed in μg/ml. Antigen-specific IgG1 was measured by ELISA using 96-well plates coated with allergen extract.

Antibody was detected with HRP-labelled anti-mouse IgG1. Results are expressed as relative 21 absorbance units (OD450).

Intracellular Cytokine Staining.

After treatment, mice were humanely sacrificed by $CO_2$ asphyxiation and their spleens removed and homogenized in PBS. The homogenate was filtered and red blood cells lysed with ammonium chloride lysing reagent (BD Pharmingen, Cowley, UK) and fixed with 4% (v/v) paraformaldehyde for 20 min. The cells were washed with PBS supplemented with 3% heat inactivated fetal calf serum with 0.1%(w/v) sodium azide (FSB), re-suspended in 10% DMSO(v/v) in FSB and stored at $-80°$ C.

Cells were permeabilized with CYTOPERM® wash buffer (CPB, BD Biosciences, Cowley, UK) for 15 min at $4°$ C. and aliquots of 106 cells were blocked by incubation for 30 min at $4°$ C. with CPB supplemented with 1% (v/v) rat IgG. Intracellular cytokines were stained with 1 μg PE-conjugated anti-mouse cytokine monoclonal antibody (BD Biosciences, Cowley, UK) incubated for 60 min at 4 vC. The cells were washed with CPB followed by FSB and re-suspended in 500 μl FSB. Flow cytometry was performed with a FACSCAN® flow cytometer (Beckton Dickinson, Mountain View, Calif., USA) using CELLQUEST® software. Data were collected for 20,000 cells. The average FSC of spleen cells was 100 in all cases. Stained cells (FSC>100, FL2>100) were gated and the proportion of these cells staining intensely for PE (PE>1000) was calculated. Results are expressed as the percentage intensely stained cells after subtraction of background fluorescence for unstained cells incubated with rat IgG (% PE>1000). For IL-4 the geometric mean fluorescence (GMF) was measured for stained cells and the background subtracted.

Lung Histology

Immediately after treatment, the lungs of 2-4 mice from each treatment group were fixed in 10% neutral buffered formalin and sent for independent analysis. Lungs were embedded in paraffin, sectioned and stained with haematoxylin and eosin (H&E). The slides were evaluated for peribronchial inflammation and scores were assigned on a scale of 0-4, corresponding to a score of normal to severe, respectively (9).

Whole Body Plethysmography

In this study, AHR was measured using unrestrained whole body plethysmography (8) with a four-chamber system (Buxco, Sharon, Conn., USA). Mice were first challenged with intranasal antigen and allowed to recover for 2 hours before being placed into the chambers and their breathing monitored for 10 min. When acclimatized, their baseline response was measured for 5 min. The mice were then subjected to 1 min of aerosolised PBS, followed by progressively increasing doses of methacholine (5, 10, 20, 30, 40 mg/ml PBS). Responses are recorded for 5 min in every case with a short interval between to allow return to baseline. Responses were quantified using the measurement of enhanced expiratory pause (Penh). Each group contained 4-8 mice. Penh is measured as the average percentage increase over the baseline value for mice in each group. Results are presented as the average percentage elevation in Penh after a challenge of methacholine. In order to determine if treatment produced a lasting effect, mice from the Der p experiment were rechallenged with allergen extract alone given intranasally, 4 days after completion of treatment.

Statistics

Results are the average for 4-8 mice/group and error bars are ±SEM. Significance was determined by Student's two tailed t-test. Significance was accepted for $p<0.05$.

Mouse Model of Pathogenic Lung Infection

Pretreatment with CMP and Pathogen Challenge

NMRI female mice were anaesthetized with ketamine/1.0 xylazine and treated daily for three days with 250 μg/μl CMP or 20 μl PBS as control. On day 0, mice were anaesthetized with ketamine/xylazine and challenged with *P. aeruginosa* $2\times10^6$ intranasally. Animal survival was measured over 10 days.

Mouse Model of Bacterial Infection

*S. pneumoniae* Preparation

*S. pneumoniae* serotype 2, strain D39, was obtained from the National Collection of Type Cultures, London, UK (NCTC 7466). Bacteria were identified as pneumococci prior to infection by Gram stain, catalase test, haemolysis on blood agar plates and by optochin sensitivity. The capsular polysaccharide serotypes were confirmed by the Quellung reaction. For use in in vivo infection experiments, pneumococci were cultured and passaged through mice as described previously (10) and subsequently stored at $-70°$ C. When required, suspensions were thawed at room temperature and bacteria harvested by centrifugation before re-suspension in sterile PBS.

Infection of Mice

Female MF1 out-bred mice, nine weeks old and weighing 30-35 g (Harlan Olac, Bichester, UK), were lightly anesthetized with 2.5% (vol/vol) flurothane® (AstraZeneca, Macclesfield, UK) over oxygen (1.5-2 liter/min). 50 μl PBS containing $1\times10^6$ cfu *S. pneumoniae* was administered into the nostrils of mice. The inoculum was confirmed by plating out on blood agar plates following infections. At hourly intervals following infection pre-selected groups of mice were deeply anaesthetised with 5% (vol/vol) fluo-thane before collection of blood by cardiac puncture. Following this procedure, the mice were killed immediately by cervical dislocation. The lung were removed into 10 ml of sterile distilled water, weighed and then homogenised in a Stomacher-Lab blender (Seward Medical, London, UK). Viable counts in homogenates and in blood were determined as before (10). The presence of type 2 polysaccharide capsule was confirmed by the Quellung reaction. These mice did not have detectable levels of anti-type 2, antitype 3 or anti-pneumolysin antibodies.

Treatment Strategy

On day -1, -2 and -3, mice were given 250 μg CMP in 50 μl sterile PBS, administered intranasally to anaesthetised mice. On day 3, mice were given the intranasal challenge with *S. pneumoniae* and sacrificed at hourly intervals.

Cytokine Production in Human Leukocytes

Effect of CMP Administration on Human Monocytes

Blood was obtained from three healthy donors and 10 U/ml heparin added as an anticoagulant. Aliquots of 0.6 ml were incubated with 10 μg/ml brefeldin A (BFA), an inhibitor of protein secretion from cells and 5 ng/ml LPS derived from Salmonella Minnesota, with or without 0.1 μg/ml CMP. Incubation was at $37°$ C. for 6 h. After incubation, red blood cells were lysed with ammonium chloride buffer and re-suspended in FACS staining buffer. Cell surface markers CD14 and CD16 were stained with fluorescent-labelled antibody, after cell permeabilization with saponin. Specificity of staining for TNFα was demonstrated by performing the intracellular cytokine staining in the presence of a 9-fold excess of recombinant human TNFα. After FACS analysis of the stained cells, the CD14 or CD14/CD16 populations were gated and results are given as the median fluorescence intensity (MFI) for TNFα staining after subtraction of the background staining for each donor.

Effect of CMP Administration on Human T-lymphocytes

Blood aliquots from two donors were incubated with BFA and 5 ng/ml PMA+0.25 µM Ionomycin as a T-cell activator in the presence or absence of 0.1 µg/ml CMP for 6 h at 37° C. T-cells were stained for surface marker CD2 and stained for IFN7 by intracellular cytokine staining.

Results

Example 1

The effect of treatment with CMP on blood eosinophilia of animals challenged with Afu, is shown in FIG. 1. Groups had received treatment for 4 days and measurements were made on day 5. The sample size was 4-5 mice/group. Error bars±SEM. The results indicate that treatment with CMP resulted in a drop in the blood eosinophilia level to ca $0.3 \times 10^6$/ml, compared with test animals treated with PBS which exhibited blood eosinophilia levels of ca $0.7 \times 10^6$/ml.

Example 2

Figure 2:
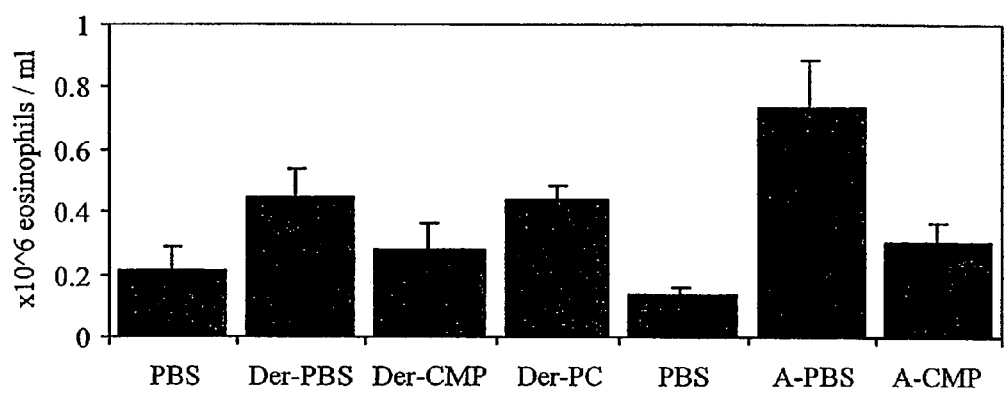
FIG. 2 shows the results of treatment of Der p and Afu challenged mice with 4 daily doses of 25 μg CMP which produced a significant decrease ($p<0.05$) in peripheral blood eosinophilia.

The effect of treatment with CMP on peripheral blood eosinophilia of mice challenged with Der p and Afu is shown in FIG. 2. Groups were challenged daily with Afu or Der p extract, given intranasally, followed by intranasal treatment with 4 daily doses of 25 µg CMP. PBS represents un-sensitised mice treated with PBS. Der-PC represents sensitised mice treated with a particulate control (PC) of latex beads. The sample size was 4-8 mice/group. Error bars±SEM. Peripheral blood eosinophilia was reduced by 36% in the Der p model and 58% in the Afu model ($p<0.05$).

Example 3

Figure 3:
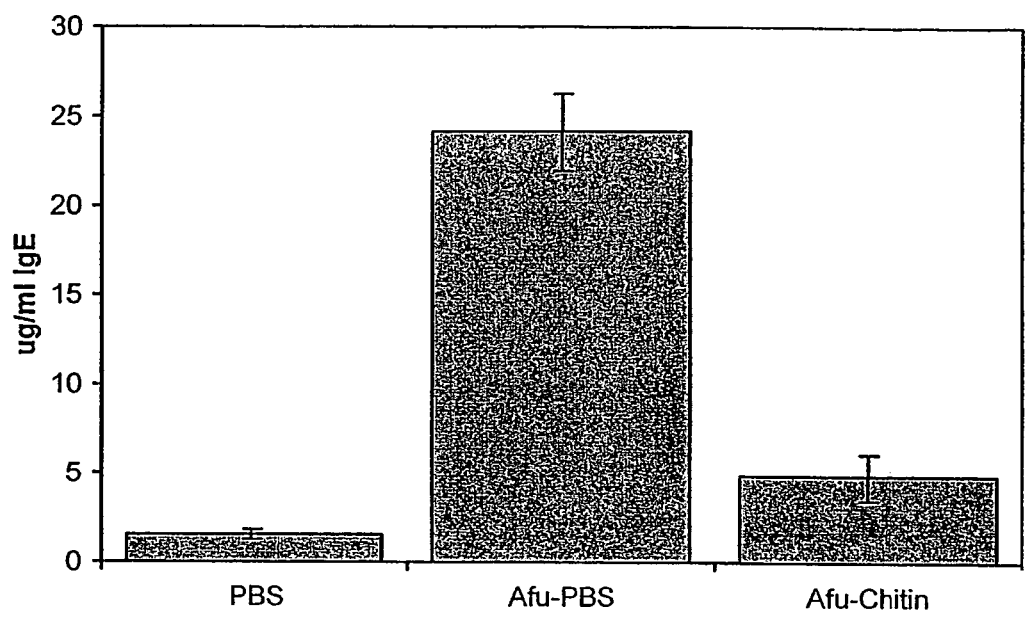
FIG. 3 shows a reduction in serum total IgE ($p<0.0005$) of Afu challenged mice, after treatment with 17 μg/day of CMP.

A comparison of the effect of treatment with CMP on serum IgE levels of mice challenged with Afu, is shown in FIG. 3. Groups were treated for 5 days and measurements were made on blood collected 3 days later.

The sample size was 4-5 mice/group. Error bars±SEM.

The results indicate that serum IgE levels 3 days after intranasal treatment with CMP (Afu-Chitin) are less than 5 µg/ml IgE, compared with 24 µg/ml IgE in sensitised animals treated with PBS (Afu-PBS). PBS represent unsensitised mice treated with PBS.

Example 4

Figure 4:
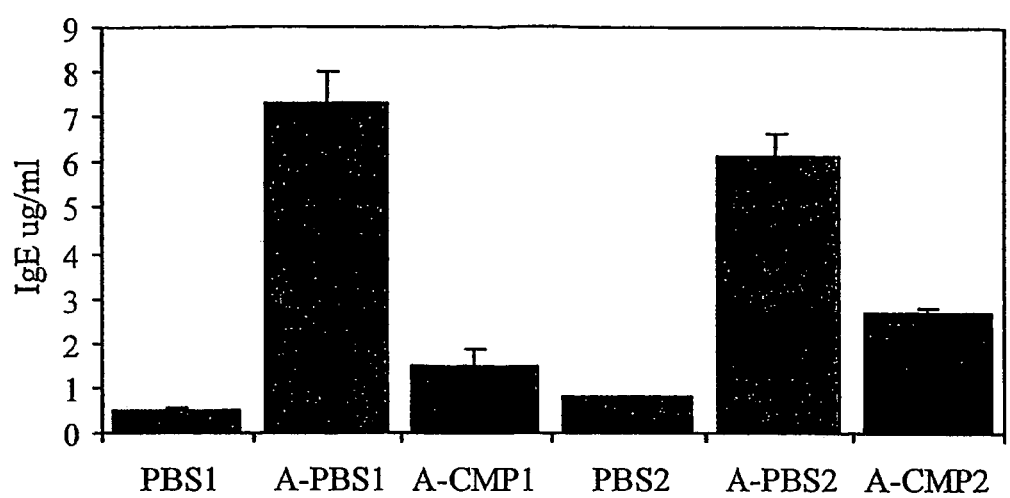
FIG. 4 shows a reduction in serum total IgE ($p<0.0005$) of Afu challenged mice, after treatment with 5 daily doses of 17 μg CMP and after re-challenge with allergen 1 week later.

The effect of treatment with CMP on serum IgE levels of mice challenged with Afu is shown in FIG. 4. Groups were challenged daily with Afu extract, given intranasally, followed by intranasal treatment with 5 daily doses of 17 Rg CMP (A-CMP1) or PBS (A-PBS1) given 1 hour afterwards. Mice were re-challenged with 3 daily intranasal doses of allergen extract given alone the following week and blood IgE levels re-measured (A-PBS2, A-CMP2). The sample size was 4-8 mice/group. Error bars±SEM. The results indicate a significant reduction in serum IgE ($p<0.0005$) which was maintained following rechallenge with allergen, one week later ($p<0.0005$).

Example 5

Figure 5:
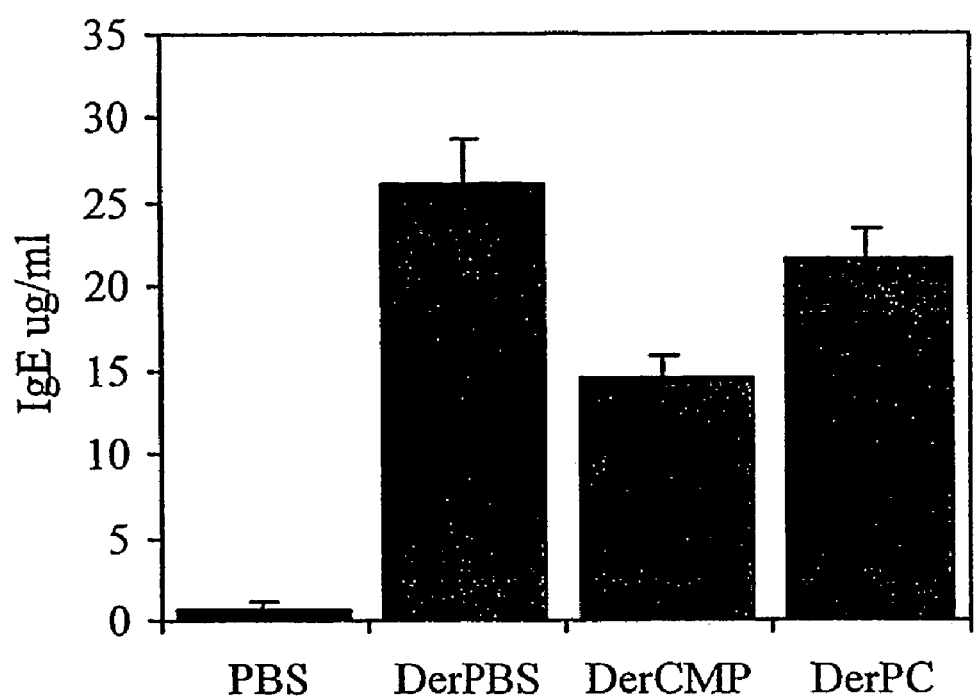
FIG. 5 shows the results of treatment of Der-p challenged mice, with 5 daily doses of 25 μg CMP which produced a significant decrease ($p<0.005$) in total serum IgE.

The effect of treatment with CMP on serum IgE levels of mice challenged with Der p, is shown in FIG. 5. Groups were challenged daily with Der p extract, given intranasally, followed by intranasal treatment with 5 daily doses of PBS (DerPBS), 25 µg CMP (DerCMP) or 25 µg or a particulate control of latex beads (DerPC). PBS represents un-sensitised mice treated with PBS, given 1 hour later. The sample size was 4-8 mice/group. Error bars±SEM. Treatment with 5 daily doses of 25 µg CMP produced a significant decrease in total serum IgE ($p<0.005$), measured 4 days after treatment.

Example 6

Figure 6:
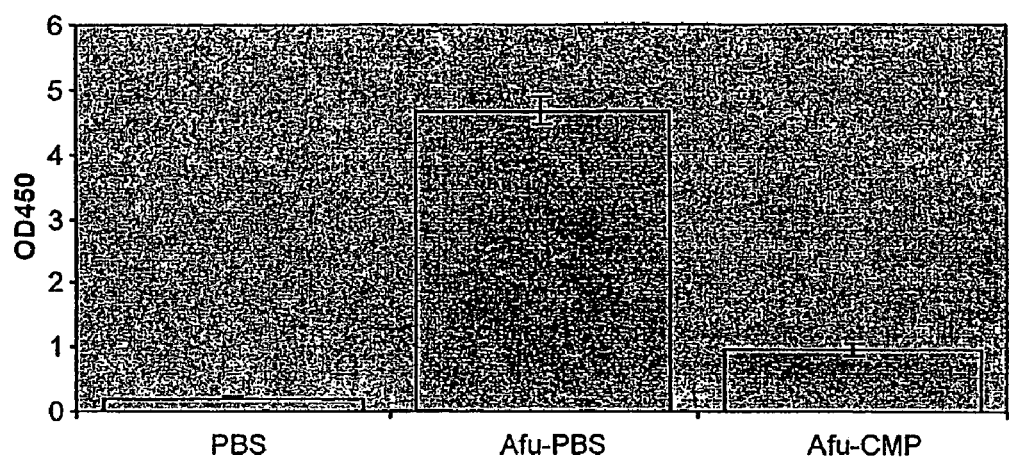
FIG. 6 shows a reduction in Afu specific IgG1 ($p<0.01$).

A comparison of the effect of treatment with CMP or PBS on serum IgG1 levels of mice challenged with Afu, is shown in FIG. 6. Groups were challenged and treated daily for 5 days with either PBS or 25 µg CMP given intranasally and measurements were made on blood collected 3 days later. The sample size was 4-5 mice/group. Error bars±SEM. Sensitised animals challenged intranasally with Afu allergen extract, followed by intranasal treatment with CMP (Afu-CMP) showed a four fold decrease in serum IgG1 levels relative to sensitised animals treated with PBS (Afu-PBS). PBS represent un-sensitised mice treated with PBS.

Example 7

Figure 7:
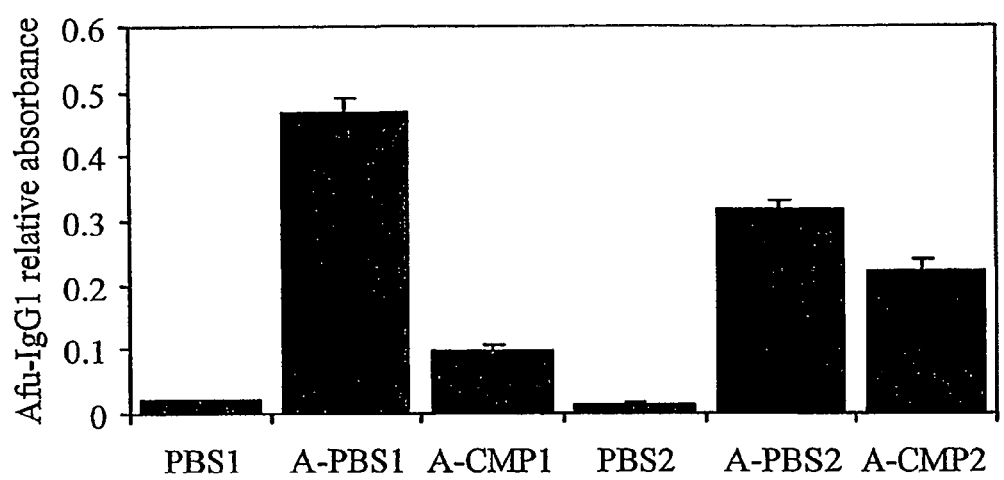
FIG. 7 shows a reduction in Afu specific IgG1 ($p<0.001$) after treatment with 5 daily doses of 17 μg CMP, and after re-challenge with allergen 1 week later.

The effect of treatment with CMP on Afu specific IgG1 levels of mice challenged with Afu, is shown in FIG. 7. Groups were challenged daily with Afu extract, given intranasally, followed by intranasal treatment with 5 daily doses of 17 µg CMP (A-CMP1) or PBS (A-PBSI) 1 hour afterwards. Mice were re-challenged with 3 doses of allergen extract alone the following week and blood IgGI levels re-measured (A-PBS2, A-CMP2). The sample size was 4-8 mice/group. Error bars±SEM. The results indicate a significant reduction in Afu-specific IgG1 ($p<0.001$) which was maintained on re-challenge with allergen, one week later ($p<0.01$).

Example 8

Figure 8:
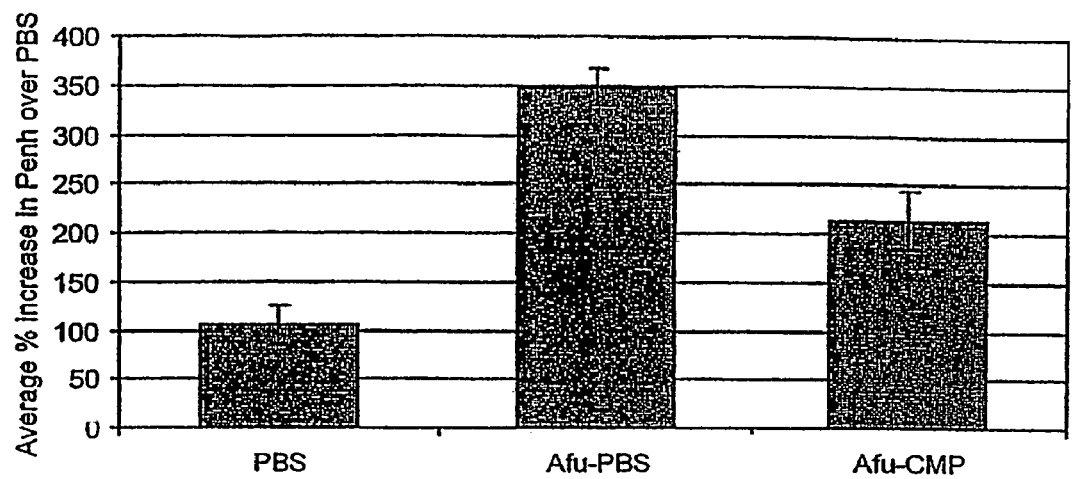
FIG. 8 shows a reduction in airway hyperresponsiveness ($p<0.01$) in mice re-challenged with the Afu antigen after treatment with CMP.

The effect of allergen re-challenge on AHR of mice challenged with Afu, is shown in FIG. 8. Groups were treated with intranasal challenges of Afu allergen followed by intranasal treatment with PBS (Afu-PBS) or 20 µg CMP (Afu-CMP) repeated daily for 4 days. Mice were re-challenged with allergen alone and AHR measured in response to provocation with 30 mg/ml of nebulized methacholine. PBS represent un-sensitised mice treated with PBS. The sample size was 4-8 mice/group. Error bars±SEM. The results indicate that AHR was significantly reduced ($p<0.01$) in animals treated with CMP. These mice showed only a 110% increase in Penh over control mice when challenged with methacholiner compared to a 240% increase for PBS treated mice.

Example 9

Figure 9:
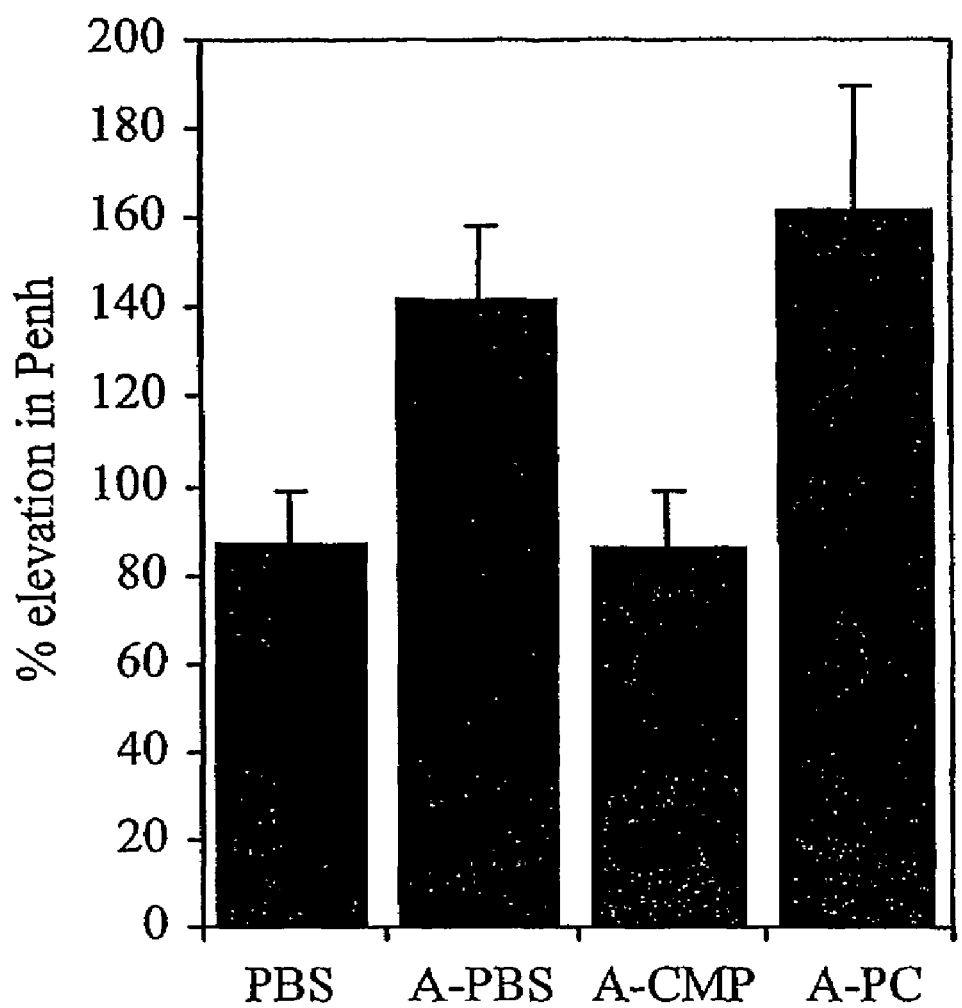
FIG. 9 shows a reduction in AHR ($p<0.01$) in mice challenged with Afu antigen, after 4 days of CMP treatment.

Airway hyperresponsiveness of mice challenged with Afu, in response to a 20 mg/ml challenge of nebulized methacholine, is shown in FIG. 9. Groups were given 4 daily doses of PBS or 25 µg CMP intranasally. The sample size was 4-8 mice/group. Error bars±SEM. A significant reduction in AHR was observed in the CMP treated group ($p<0.01$). Treatment with the particulate control of latex beads (A-PC) did not reduce AHR.

Example 10

Figure 10:
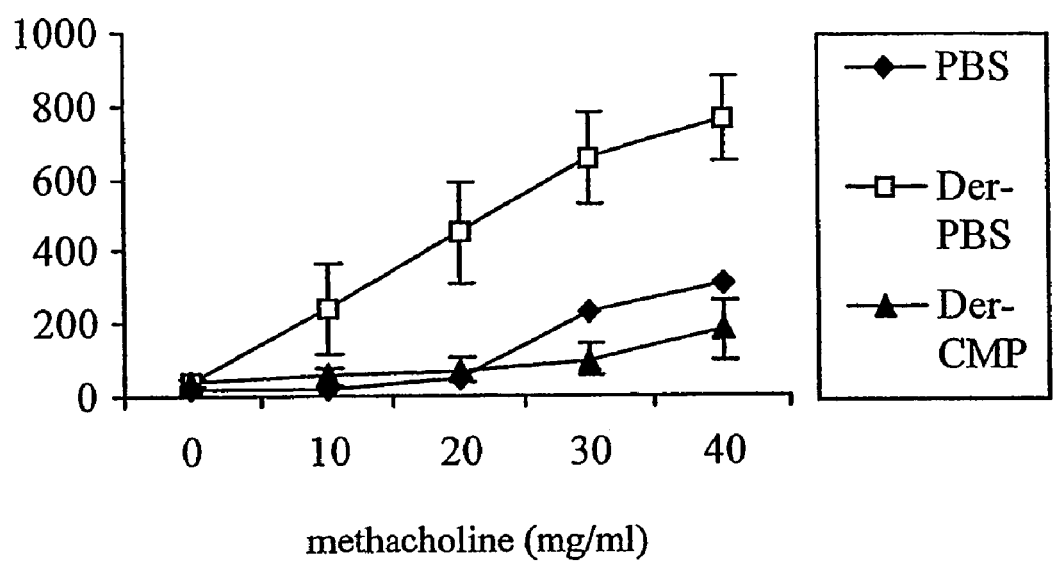
FIG. 10 shows a reduction in AHR, in mice challenged with the Der p antigen after treatment with CMP, to increasing concentrations of methacholine.

A dose response of treatment groups challenged with Der p to nebulized methacholine is shown in FIG. 10. Groups were first given an intranasal challenge of Der p extract followed by intranasal treatment with PBS (Der-PBS) or 25 Vtg CMP (Der-CMP), repeated for 4 days. Mice were rechallenged with Der p 4 days after completion of the challenge/treatment course. AHR was measured in response to different doses of nebulized methacholine. PBS represent unsensitised mice treated with PBS. The sample size was 4-8 mice/group. Error bars±SEM. The results indicate a reduced AHR to all concentrations of methacholine tested.

Example 11

Figure 11:
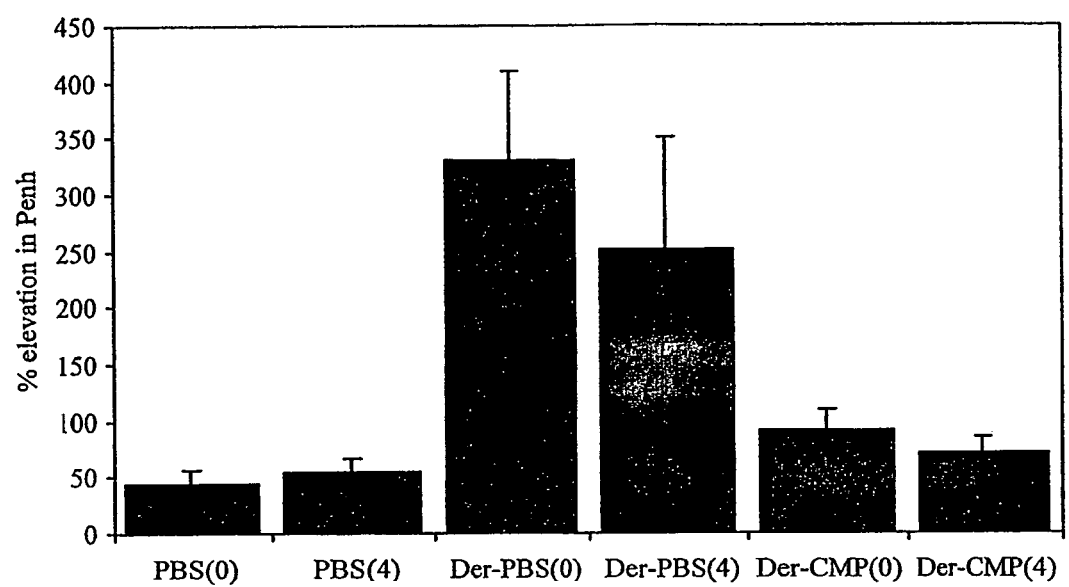
FIG. 11 shows a reduction in AHR 3 days after treatment with 25 μg CMP preceded by allergen challenge (Der-CMP (O), $p<0.001$) and re-challenge 4 days later (Der-CMP(4), $p<0.001$).

AHR of mice challenged with Der p in response to nebulized methacholine is shown in FIG. 11. Groups were treated for 3 days with 25 µg CMP intranasally, preceded by allergen challenge (Der p(O)) and rechallenged with allergen alone 4 days after completion of treatment with a total of 4 daily doses of 25 µg CMP preceded by allergen challenge (Der-CMP(4)). PBS represent unsensitised mice treated with PBS. Results are expressed as the elevation of Penh and show a significant reduction in AHR on the fourth day of treatment (Der-CMP (O), $p<0.001$) and after re-challenge 4 days after treatment (Der-CMP(4), $p<0.001$).

Example 12

Figure 12:
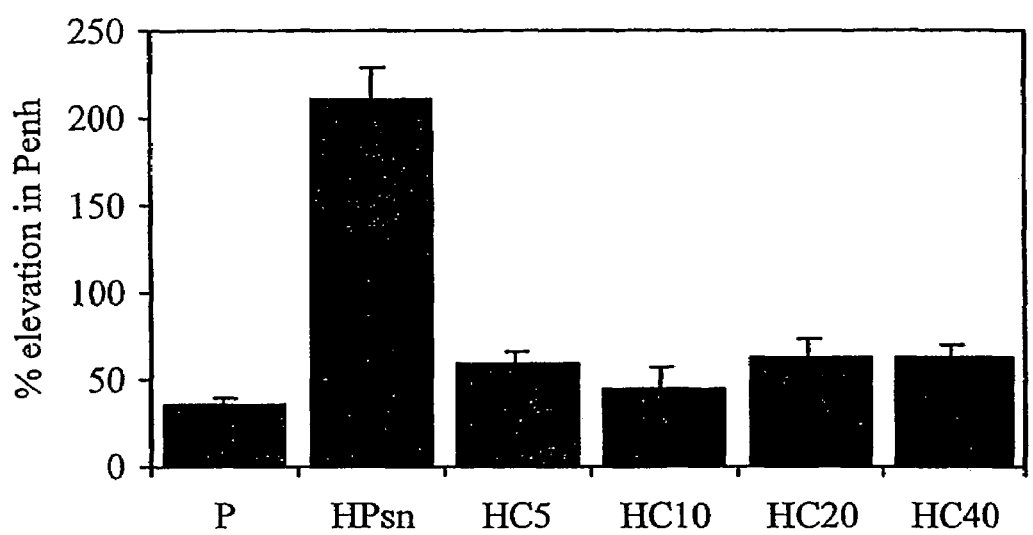
FIG. 12 shows a reduction in AHR in mice challenged with Der p, after 4 days of treatment with varying doses of CMP, in response to methacholine exposure.

AHR of Der p (H=Der p) sensitised mice treated with CMP is shown in FIG. 12. Groups were treated for 4 days with four different doses of CMP (5-40 µg). On day 4 mice were challenged with Der p and treated 1-2 h later with CMP or a control treatment of the CMP supernatant, free of any CMP, from a 25 µg/ml suspension (Psn). AHR was measured after exposure to 100 mg/ml nebulized methacholine for 1.5 min. P represents non-sensitised mice. Results show all doses of CMP were equally effective and suggest that a dose of five fold lower than that used in previous experiments can be used to prevent an allergic response in this model.

Example 13

Figure 13:
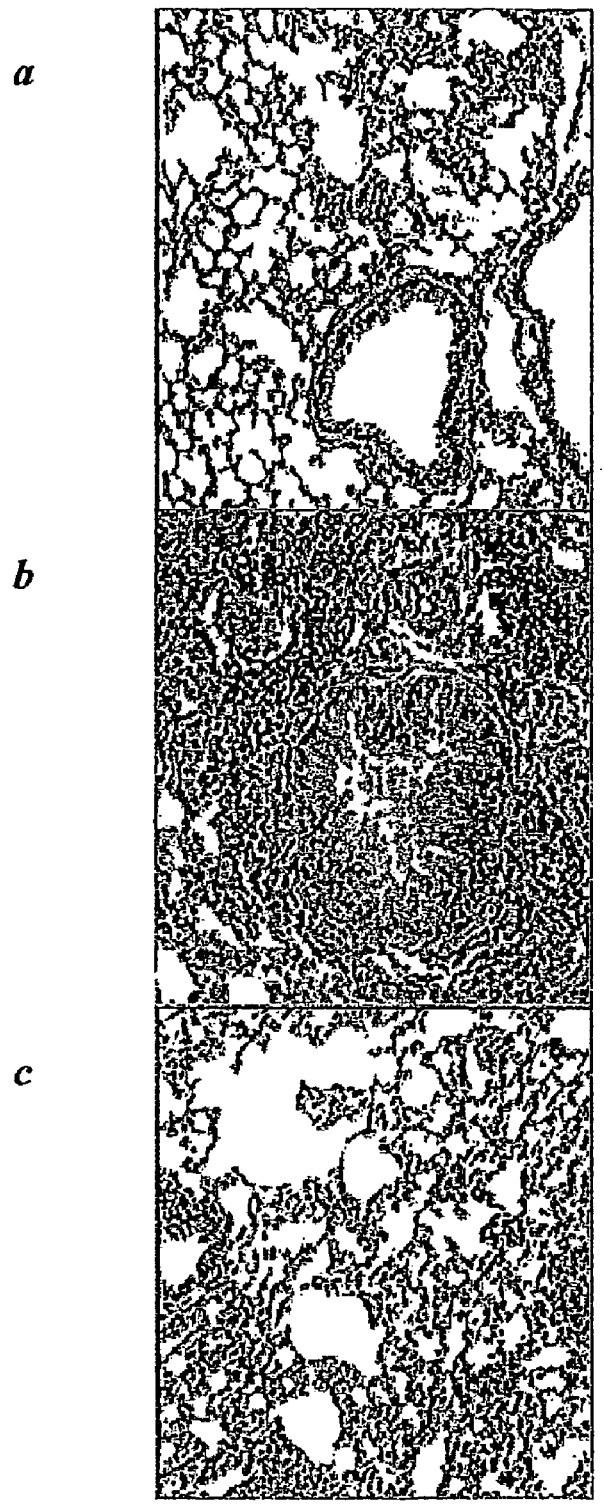
FIG. 13 shows lung sections differing in the degree of inflammation and obstruction after CMP treatment of Afu sensitised mice.

Lung sections stained with haematoxylin and eosin, illustrating the differences in the degree of inflammation and obstruction of airways after treatment of Afu sensitised mice with CMP, are shown in FIG. 13. The peribronchial inflammation of allergen challenged mice treated with PBS gave an average score of 2.5 compared with a score of 1 for CMP treated mice also challenged with allergen. This represents a 60% reduction in allergen induced inflammation. Nonsensitised mice treated with PBS gave a score of 0. FIG. 13a shows normal mouse lung after treatment with PBS, 13b shows allergic lung treated with PBS and 13c shows allergic lung after intranasal treatment with 4 daily doses of 25 µg CMP.

Example 14

The effect of treatment on IL-12, IFN-γ. TNFα and IL-4 levels in Der-p and Afu challenged mice is shown in Table 1a. Groups were given 4 daily doses of allergen extract followed by intranasal treatment with 25 µg CMP or a nonspecific particulate control of polystyrene microbeads (PC). Cytokine producing activity was assessed by measuring the proportion of highly stained cells positive for the respective anti-cytokine antibody labelled with phycoerythrin. Results are shown±SEM. IL-12 was significantly elevated by 77% (Der-CMP, $p<0.005$) in the Der p model and elevated by 43% (Afu-CMP) in the Afu model. The particulate control did not elevate IL-12 levels. IFN-γ was significantly elevated by 41% (DerCMP, $p<0.05$) in the Der p model and by 22% (Afu-CMP, $p<0.005$) in the Afu model. TNF-a was significantly elevated by 44% (Der-CMP, $p<0.05$) in the Der p model and by 22% (Afu-CMP, $p<0.05$) in the Afu model. The effect of treatment on GM-CSF levels in Der p challenged mice is shown in Table 1b. Mice were treated with 40 µg CMP. GM-CSF was measured by intracellular cytokine staining and flow cytometry. Treatment with CMP produced a significant ($p<0.05$) decrease in GM-CSF relative to treatment with PBS alone and approached the levels seen in non-allergic naive mice. Comparison of the geometric mean fluorescence (GMF) of spleen cells stained for IL-4 (Table 1c) showed a decrease of 34% (Der-CMP) in the Der p model and 27% (Afu-CMP) in the Afu model. No decrease was observed with the particulate control.

Example 15

Figure 14:
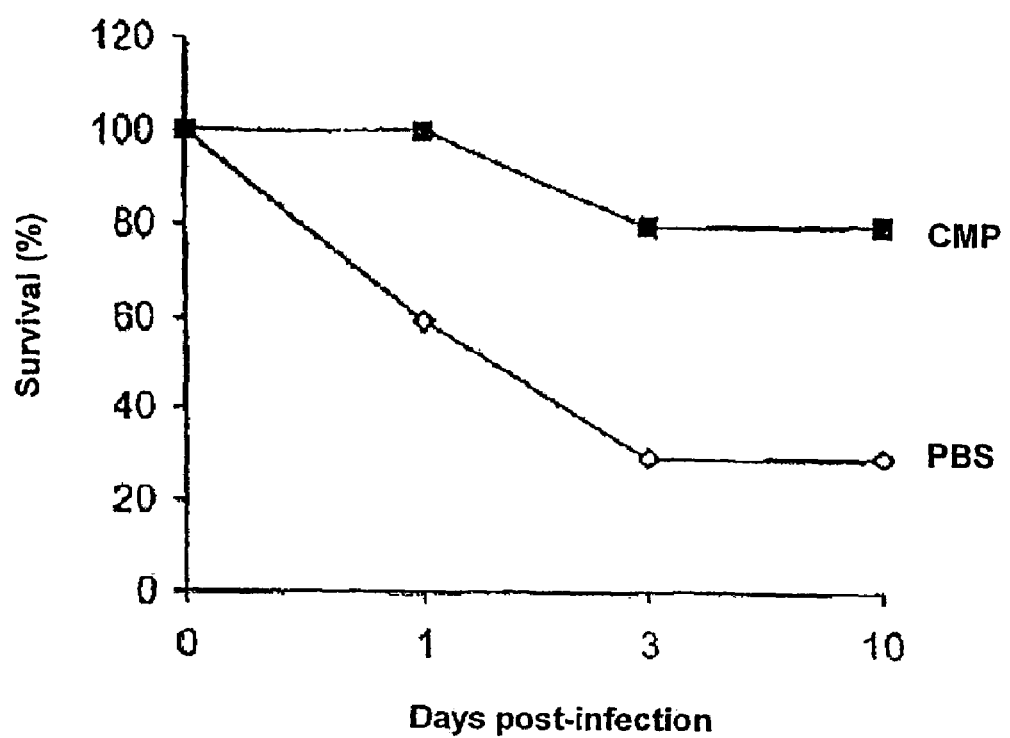
FIG. 14 shows the survival of mice pretreated with CMP or control (PBS), in response to *P. aeruginosa* infection.

The effect of pre-treatment with CMP on *P. aeruginosa* infected mice is shown in FIG. 14. Mice were pretreated for three days with 250 µg CMP in PBS, intranasally, before intranasal infection with $2\times10^6$ *P. aeruginosa*. Animal survival was measured for 10 days. The experiment was performed twice and the results combined. One day after pathogen challenge 40% of the control treated mice had died whereas, in contrast, the CMP treated mice showed a 100% survival rate. Three days after pathogen challenge, 70% of the control treated mice had died, whereas the CMP treated mice exhibited a 80% survival rate. No change in these survival rates was observed up to 10 days after infection.

Example 16

Figure 15:
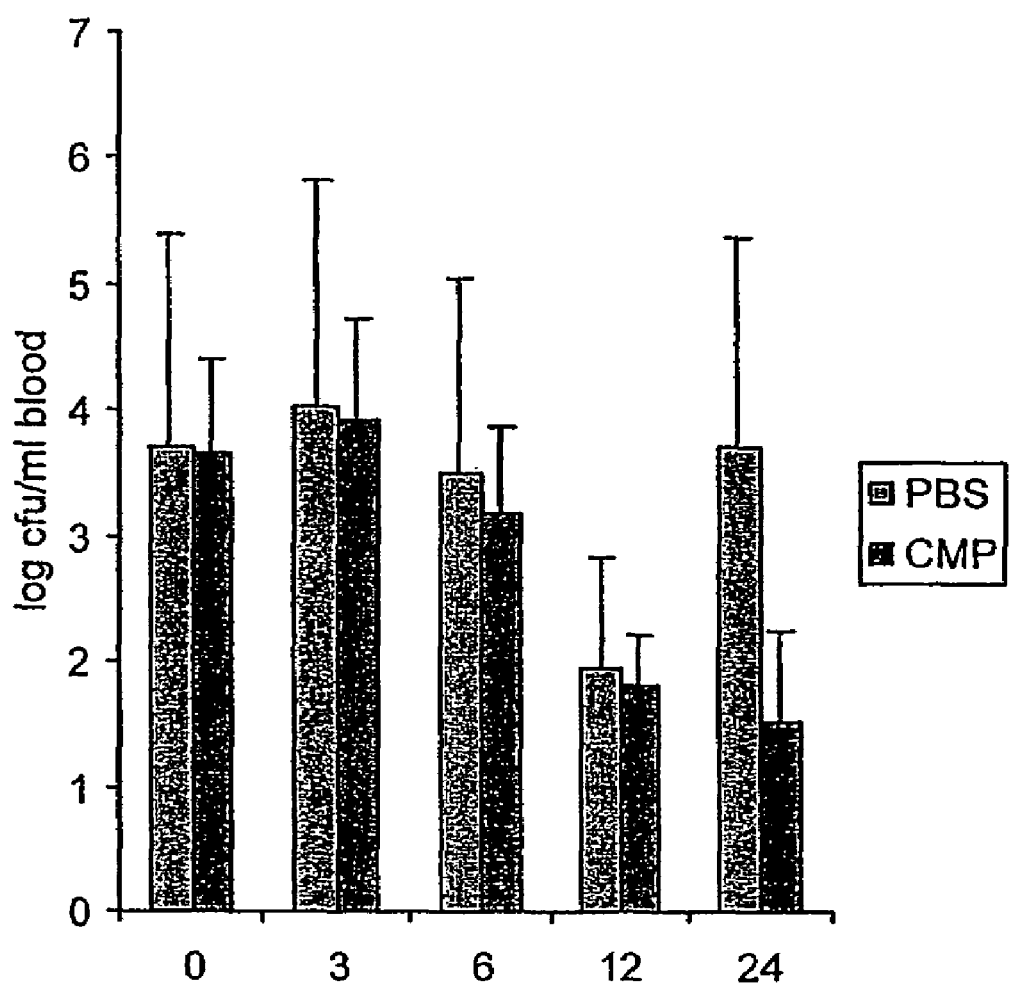
FIG. 15 shows the time-course for the clearance of *S. pneumoniae* from infected murine lung.

The effect of 250 µm CMP pre-treatment on lung clearance of *S. pneumoniae* in mice is shown in FIG. 15. No difference was observed between PBS and CMP treated mice from 0-12 h; however at the 24 h time point CMP treated mice had significantly lower bacterial cfu in the lungs ($P<0.001$).

Example 17

Figure 16:
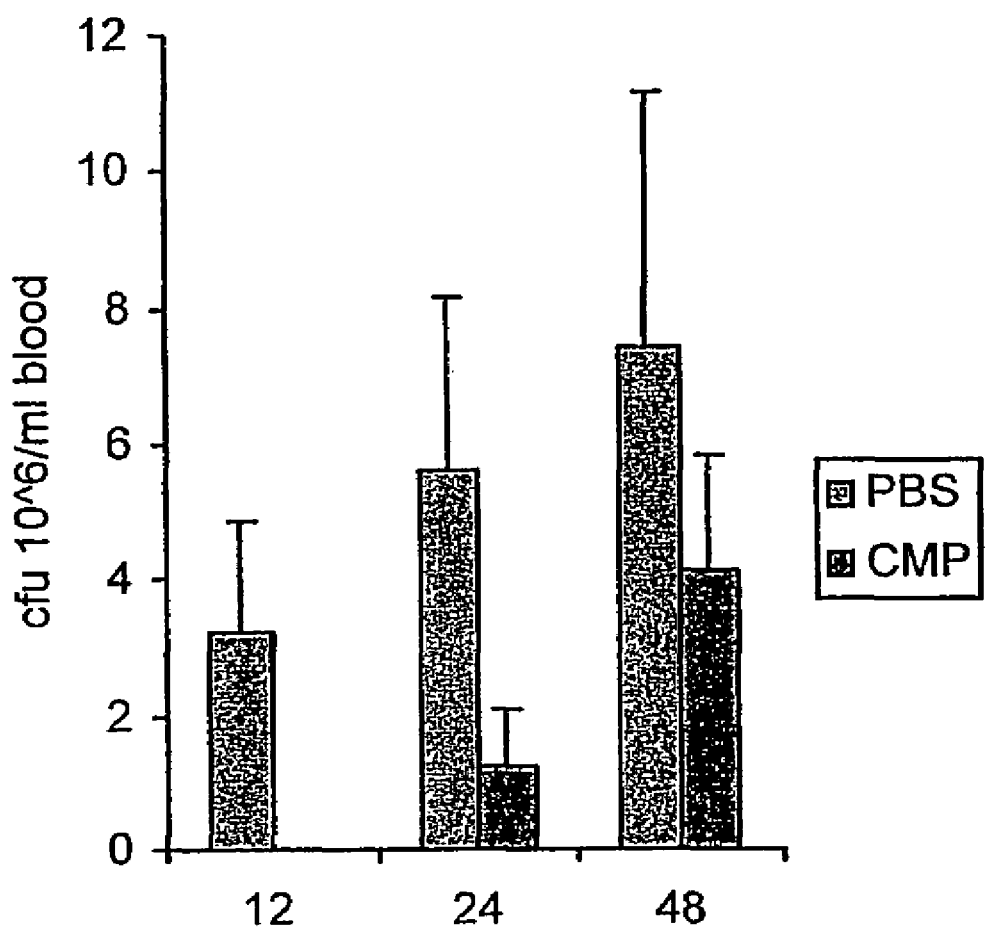
FIG. 16 shows the time-course for the appearance of *S. pneumoniae* in the blood of infected mice.

The effect of 250 pm CMP pre-treatment on the appearance of *S. pneumoniae* in the blood of infected mice is shown in FIG. 16. No bacteria were observed at the 12 h time point and blood bacteraemia was significantly less at 24 h ($p<0.005$) and 48 h, suggesting that CMP is protective in the lungs by 12-24 h.

Example 18

Figure 17:
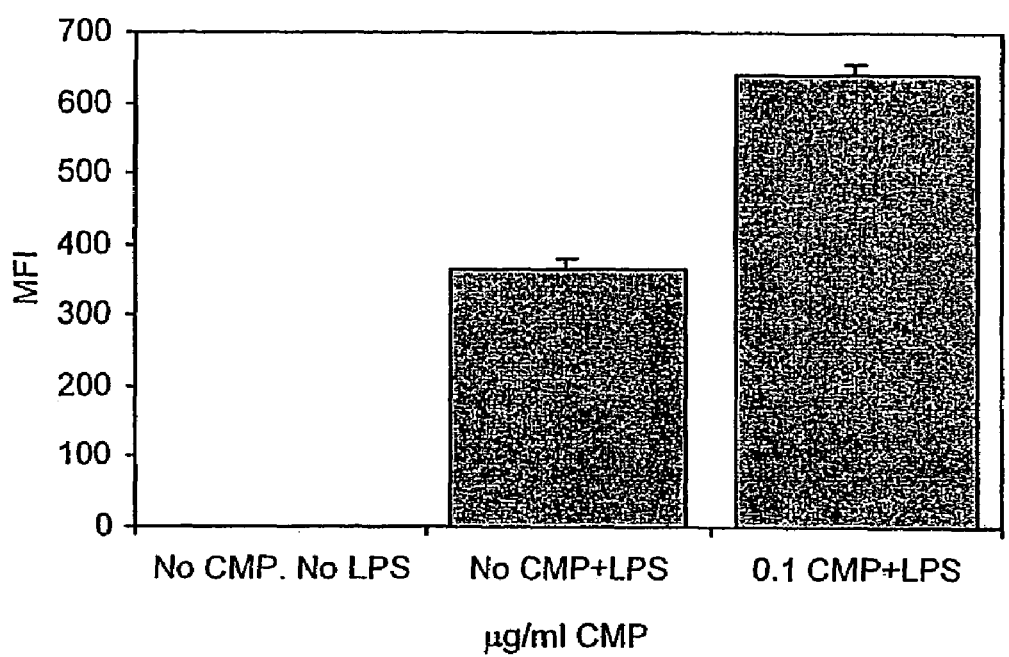
FIG. 17 shows the enhancement by CMP on TNFα production by LPS activated CD14 monocytes.

The effect of 0.1 µg/ml CMP on TNFα production in LPS activated CD14 human monocytes is shown in FIG. 17. There was very little production of TNFa by monocytes incubated with 0.14 g/ml CMP alone. However incubation of blood with 0.1 gg/ml CMP supplemented with 5 ng/ml LPS as a 33 monocyte activator resulted in a significant ($p<0.001$) elevation in TNFa production measured in the CD14+ monocytes when compared to the cells stimulated with LPS alone.

Example 19

Figure 18:
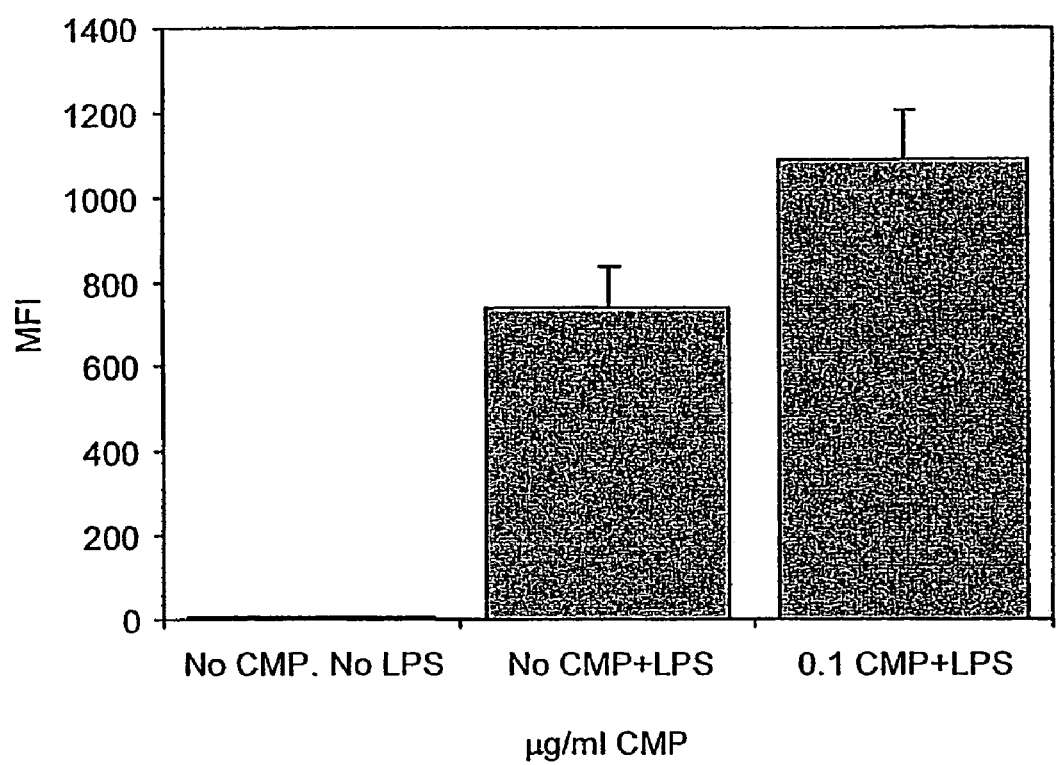
FIG. 18 shows the enhancement by CMP on TNFα production by LPS activated CD14/CD16 proinflammatory monocytes.

The effect of 0.1 µg/ml CMP on TNFα production in LPS activated CD14/CD16 proinflammatory human monocytes is shown in FIG. 18. There was little production of TNFα in proinflammatory monocytes incubated without CMP or LPS. Incubation with 0.1 µg/ml CMP supplemented with 5 ng/ml LPS resulted in an elevation in TNFα, production of approximately 350 MFI, when compared to the cells stimulated with LPS alone.

Example 20

Figure 19:
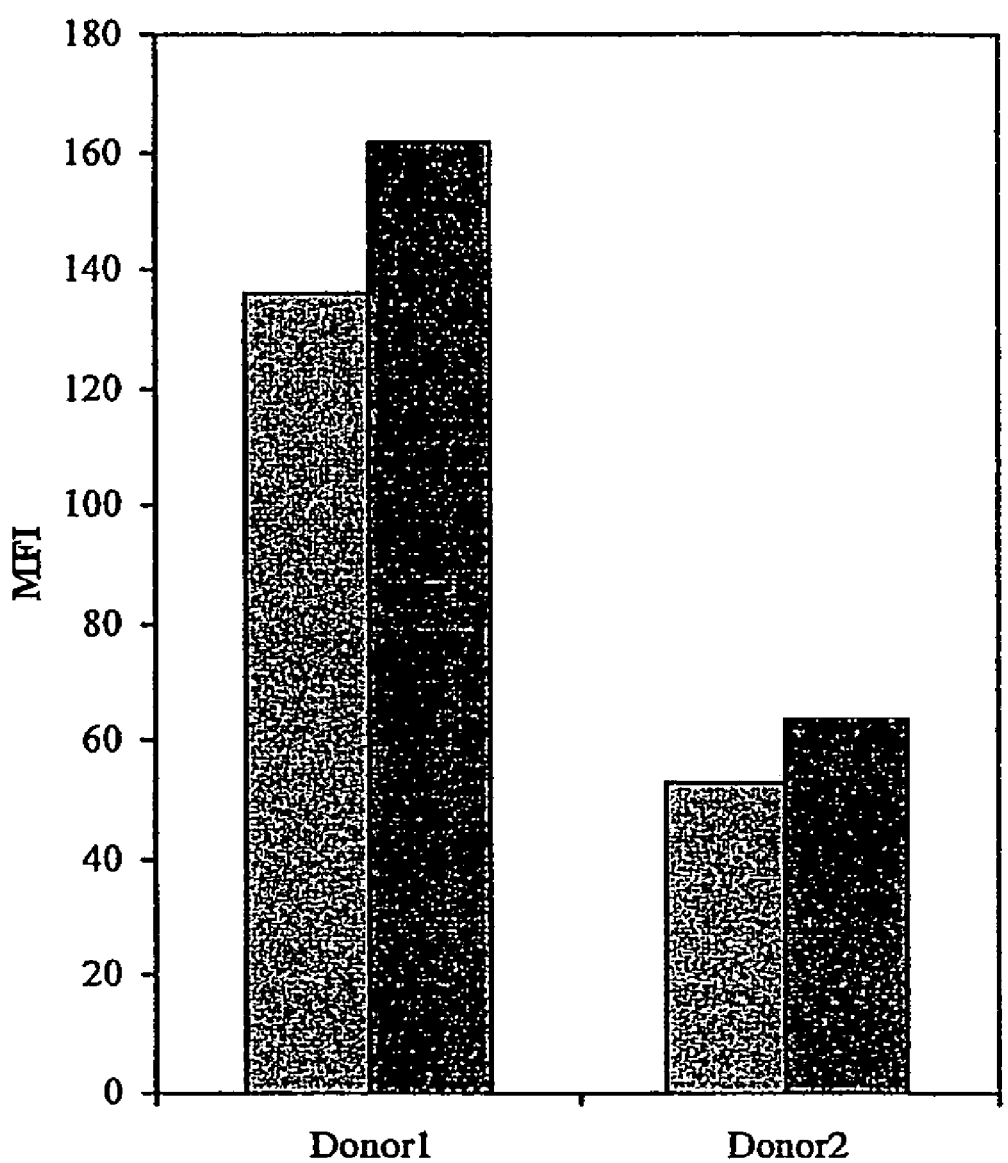
FIG. 19 shows enhanced production of IFNγ from PMA/Ionomycin stimulated human T-lymphocytes by CMP.

The production of IFNγ from PMA/Ionomycin stimulated human T-lymphocytes by 0.1 µg/ml CMP is shown in FIG. 19. The addition of CMP elevated the production of IFNγ by 20% from PMA/Ionomycin stimulated CD2+ T-lymphocytes cultured in vitro. The results indicate that CMP are able to promote the activity or proliferation of Th1 lymphocytes.

Further Aspects of the Invention

Further aspects of the invention are now set out in the following numbered paragraphs; it is to be understood that the invention encompasses these aspects:

Paragraph 1. Use of a chitin microparticle preparation (CMP) for the preparation of a medicament for the treatment of allergy, wherein the medicament is delivered intranasally or by inhalation and the chitin microparticles have an average diameter of less than 10 µm.

Paragraph 2. The use of paragraph 1, wherein the allergy is seasonal respiratory allergies; allergy to aeroallergens; allergy treatable by reducing serum IgE and eosinophilia; asthma; eczema; food allergy; dermatitis; or the treatment of allergy by allergic desensitisation.

Paragraph 3. The use of paragraph 2, wherein the aeroallergen is house mite dust, fungal spores, grass pollens, tree pollens or animal danders.

Paragraph 4. The use of paragraph 2 wherein the dermatitis is atopic dermatitis.

Paragraph 5. The use of paragraph 1, wherein the chitin microparticle composition is for allergic desensitisation and further comprises an allergen.

Paragraph 6. The use of paragraph 5, wherein the allergen is a food allergen.

Paragraph 7. The use of paragraph 6, wherein the food allergen is found in milk, wheat, gluten, eggs, nuts or shellfish.

Paragraph 8. The use of paragraph 1, wherein the medicament is used to treat an animal.

Paragraph 9. The use of paragraph 8. wherein the animal is a horse and the allergy is asthma or is associated with recurrent lung infection.

Paragraph 10. Use of a chitin microparticle (CMP) preparation for the preparation of a medicament for the treatment of conditions benefiting from up-regulation of the cellmediated immune system, wherein the medicament is administered intranasally or by inhalation and the chitin microparticles have an average diameter of less than 10 µm.

Paragraph 11. The use of paragraph 10, wherein the condition benefiting from up-regulation of the cell-mediated immune system is a bacterial infection, a fungal infection or a viral infection.

Paragraph 12. The use of paragraph 11, wherein the infection is an ear, nose, throat or lung infection.

Paragraph 13. The use of any one of paragraphs 10 to 12, wherein the medicament is used for the treatment of a patient at risk of developing an infection.

Paragraph 14. The use of paragraph 13, wherein the patient at risk is an elderly person, a premature baby, an infant, a transplantation patient, an immunosuppressed patient a chemotherapy patient, a hospital patient at risk of opportunistic infection a patient on a ventilator, a cystic fibrosis patient or a patient with AIDS.

Paragraph 15. The use of any one of paragraphs 11 to 14, wherein the condition is a bacterial infection by *Pseudomonas aeruginosa*, a *Streptococcus* species, *Haemophilus influenza*, *Klebsiella pneumoniae*, *Yersinia enteocolitica*, *Salmonella*, *Listeria*, a *Mycobacteria* species or a parasitic infection.

Paragraph 16. The use of paragraph 15, wherein the *Streptococcus* species is *Streptococcus pneumoniae*, *Streptococcus pyrogenes* or *Streptococcus agalactiae*.

Paragraph 17. The use of paragraph 15, wherein the *Mycobacterial* species is *Mycobacterium tuberculosis* or *Mycobacterium leprae*.

Paragraph 18. The use of paragraph 15, wherein the parasitic infection is an infection by a *Leishmania* species and *Schistosoma* species.

Paragraph 19. The use of any one of paragraphs 11 to 14, wherein the condition is bacterial pneumonia such as ventilator-associated pneumonia or cystic fibrosis associated infections.

Paragraph 20. The use of any one of paragraphs 11 to 14, wherein the condition is Otitis media.

Paragraph 21. The use of any one of paragraphs 11 to 14, wherein the fungal infection is invasive pulmonary aspergillosis and invasive pulmonary candidiasis, *Pneumocystis carinii* pneumonia, or a *Coccidioides* or *Crytococcus*.

Paragraph 23. The use of any one of paragraphs 11 to 14, wherein the condition is a pulmonary viral infection.

Paragraph 24. The use of any one of paragraphs 11 to 14, wherein the viral infection is caused by infection by respiratory syncytial virus bronchiolitis, influenza virus, rhino virus or human immunodeficiency virus (HIV).

Paragraph 25. Use of a chitin microparticle preparation for the preparation of a medicament for the treatment of a condition by up-regulating of the activity of NK cells and/or secretion of IFN-y by cells of the immune system, wherein the medicament is administered intranasally or by inhalation and the chitin microparticles have an average diameter of less than 10 µm.

Paragraph 26. The use of paragraph 25, wherein the condition is cancer.

Paragraph 27. The use of paragraph 25, wherein the condition is lung cancer, lung carcinoma or nasal-pharyngeal carcinoma.

Paragraph 28. The use of paragraph 25, wherein the condition is a chronic lung disorder.

Paragraph 29. The use of any one of the preceding paragraphs, wherein the medicament is administered prophylactically.

Paragraph 30. The use of any one of the preceding paragraphs, wherein the chitin microparticles have an average diameter of less 5 µm.

Paragraph 31. The use of any one of the preceding paragraphs, wherein the chitin microparticles have an average size of at least 1 µm in diameter.

Paragraph 32. The use of any one of the preceding paragraphs, wherein the chitin microparticles are derived from the exoskeletons of crab, shrimp, lobster, cuttlefish, and insects and fungi.

Paragraph 33. The use of any one of the preceding paragraphs, wherein the chitin microparticles are obtainable by sonicating or milling purified chitin.

Paragraph 34. The use of any one of the preceding paragraphs, wherein the chitin microparticles are obtainable by coating carrier particles with N-Acetyl-D-Glucosamine, chitin or a fragment thereof.

Paragraph 35. The use of any one of the preceding paragraphs, wherein the medicament is administered to a patient in a therapeutically effective amount of between 0.01 and 100 mg of active compound per kg of body weight.

Paragraph 36. The use of any one of the preceding paragraphs wherein the medicament is administered to humans.

Paragraph 37. The use of any one of the preceding paragraphs wherein the chitin microparticle preparation comprises one or more of a pharmaceutically acceptable excipient, a carrier, a propellant, a buffer, a stabiliser, an isotonicizing agent, a preservative or an antioxidant.

Paragraph 38. A delivery device for the administration of the chitin microparticles of any one of the preceding paragraphs, comprising:
 a) a reservoir of chitin microparticles having an average diameter of less than 10 µm;
 b) a delivery orifice adapted to locate in a patient's mouth or nose; and
 c) a valve between the reservoir and the delivery orifice such that the valve can be operated to control delivery of the chitin microparticles.

Paragraph 39. A composition comprising a chitin microparticle composition and an allergen, wherein the chitin microparticles have a diameter of less than 10 µm.

Paragraph 40. The composition of paragraph 39, wherein the allergen is a food allergen.

Paragraph 41. The composition of paragraph 40, wherein the food allergen is an allergen found in milk, wheat, gluten or eggs.

Paragraph 42. A composition comprising a chitin microparticle composition and an allergen, wherein the chitin microparticles have a diameter of less than 10 µm for use in a method of medical treatment.

Paragraph 43. A kit comprising: (a) a chitin microparticle composition wherein the chitin microparticles have a diameter of less than 10 µm; and (b) an allergen; for simultaneous or sequential administration to a patient.

REFERENCES

The references mentioned herein are all expressly incorporated by reference.

1. Shibata et al, J. Immunol.,164: 1314-1321, 2000.
2. Shibata et al, J. Immunol., 161: 4283-8, 1998.
3. Shibata et al. Infection and Immunity, 65 (5): 17341741r 1997.
4. Shibata et al, J. Immunol., 159: 2462-2467, 1997.
5. Horan et al, Mor. Mortal. Wkly. Rep. CDC Surveill. Summ., 35: 17SS-29SS, 1986.
6. Davies J., Nature, 383: 219-220, 1996.
7. Arruda et al, J. Immunol. 149:3354-9, 1992.
8. Hamelmann et al, Am. J. Respir. Crit. Care Med. 156. 766.775r 1997.
9. Sur et al, J. Immunol., 162: 6284-6293, 1999.
10. Kadioglu et al, Infect. Immun., 2: 492 2000.

What I claim is:

1. A method of nasally treating an allergy in a patient comprising intranasally administering to the nasal mucosa of the patient a therapeutically effective amount of between 0.01 and 100 mg per kg of body weight of the patient of chitin microparticles in a chitin microparticle (CMP) preparation to stimulate cell-mediated immunity and anti-inflammatory responses in the nasal tissue, wherein the CMP preparation comprises chitin microparticles that are insoluble in a pharmaceutically acceptable excipient or carrier and have an average diameter of less than 10 µm, and the allergy is seasonal respiratory allergies, allergies to aeroallergens, or asthma.

2. The method of claim 1, wherein the aeroallergen is selected from the group consisting of house mite dust, fungal spores, grass pollens, tree pollens and animal danders.

3. The method of claim 1, wherein the chitin microparticle preparation is for allergic desensitisation and further comprises an allergen.

4. The method of claim 1, wherein the patient is a non-human animal.

5. The method of claim 4, wherein the non-human animal is a horse and the allergy is asthma or is associated with recurrent lung infection.

6. The method of claim 1, wherein the CMP preparation is administered prophylactically.

7. The method of claim 1, wherein the chitin microparticles have an average diameter of less 5 µm.

8. The method of claim 1, wherein the chitin microparticles have an average diameter of at least 1 µm.

9. The method of claim 1, wherein the chitin microparticles are derived from the exoskeletons of crab, shrimp, lobster, cuttlefish, insects or fungi.

10. The method of claim 1, wherein the chitin microparticles are obtainable by sonicating or milling purified chitin.

11. The method of claim 1, wherein the chitin microparticles are obtainable by coating carrier particles with N-Acetyl-D-Glucosamine, chitin or a fragment thereof.

12. The method of claim 1, wherein the patient is a human.

13. The method of claim 1, wherein the chitin microparticle preparation further comprises one or more of a pharmaceutically acceptable propellant, buffer, stabiliser, isotonicizing agent, preservative or antioxidant.

* * * * *